(12) United States Patent
Sakamoto et al.

(10) Patent No.: US 9,234,056 B2
(45) Date of Patent: Jan. 12, 2016

(54) POLYMERIZABLE COMPOUND, POLYMERIZABLE COMPOSITION, POLYMER, AND OPTICALLY ANISOTROPIC BODY

(75) Inventors: Kei Sakamoto, Tokyo (JP); Kumi Okuyama, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 268 days.

(21) Appl. No.: 14/111,336

(22) PCT Filed: Apr. 12, 2012

(86) PCT No.: PCT/JP2012/060011
§ 371 (c)(1),
(2), (4) Date: Dec. 23, 2013

(87) PCT Pub. No.: WO2012/141245
PCT Pub. Date: Oct. 18, 2012

(65) Prior Publication Data
US 2014/0107247 A1    Apr. 17, 2014

(30) Foreign Application Priority Data

Apr. 15, 2011 (JP) ................................. 2011-091291
Jun. 6, 2011 (JP) ................................. 2011-126349
Dec. 14, 2011 (JP) ................................. 2011-273518

(51) Int. Cl.
*C09K 19/34* (2006.01)
*C08F 28/06* (2006.01)
*C09K 19/32* (2006.01)
*C07D 333/58* (2006.01)
*C07D 317/58* (2006.01)
(Continued)

(52) U.S. Cl.
CPC .............. *C08F 28/06* (2013.01); *C07C 251/88* (2013.01); *C07D 209/56* (2013.01); *C07D 209/86* (2013.01); *C07D 277/82* (2013.01); *C07D 317/58* (2013.01); *C07D 333/58* (2013.01); *C08F 24/00* (2013.01); *C08F 26/06* (2013.01); *C09K 19/32* (2013.01); *C09K 19/322* (2013.01); *C09K 19/3477* (2013.01); *C09K 19/3491* (2013.01); *C09K 19/3497* (2013.01); *C08F 222/1006* (2013.01); *C09K 2019/0444* (2013.01); *C09K 2019/0448* (2013.01); *C09K 2019/3408* (2013.01); *G02B 5/3083* (2013.01)

(58) Field of Classification Search
CPC .......... C08F 28/06; C08F 24/00; C08F 26/06; C07F 222/1006; C07D 209/56; C07D 209/06; C07D 317/58; C07D 333/58; C07D 227/82; C07C 251/88; C09K 19/34897; C09K 19/3419; C09K 19/32; C09K 19/322; C09K 19/3477; C09K 2019/0444; C09K 2019/0448; C02B 5/3083

See application file for complete search history.

(56) References Cited

U.S. PATENT DOCUMENTS 5,567,349 A    10/1996 Kelly et al.
6,139,771 A    10/2000 Walba et al.
(Continued)

FOREIGN PATENT DOCUMENTS

JP    10-68816 A    3/1998
JP    10-90521 A    4/1998
(Continued)

OTHER PUBLICATIONS

PCT/ISA/210—International Search Report for PCT/JP2012/060011 dated Jul. 24, 2012.

*Primary Examiner* — Sanza McClendon
(74) *Attorney, Agent, or Firm* — Birch, Stewart, Kolasch & Birch, LLP

(57) ABSTRACT

The invention provides a polymerizable compound represented by formula (I), a polymerizable composition, and a polymer that have a practical low melting point, can be produced at low cost, and can produce an optical film that achieves uniform conversion of polarized light over a wide wavelength band, and an optically anisotropic article. In the formula: $Y^1$-$Y^6$ represent a single bond, —O—, —O—C(=O)—, —C(=O)—O—, or the like; $G^1$ and $G^2$ represent a bivalent aliphatic group, or the like, of C1-20; $Z^1$ and $Z^2$ represent a C2-10 alkenyl group or the like; $A^x$ represents a C2-30 organic group, or the like, having at least one aromatic ring selected from an aromatic hydrocarbon ring and a heteroaromatic ring; $A^y$ represents a hydrogen atom, a C1-6 alkyl group, or a C2-30 organic group, or the like, having at least one aromatic ring selected from an aromatic hydrocarbon ring and a hetero-aromatic ring; $A^1$ represents a trivalent aromatic group or the like; $A^2$ and $A^3$ represent a bivalent aromatic group or the like; $Q^1$ represents a hydrogen atom, a C1-6 alkyl group, or the like. $A^x$ and $A^y$ may form a ring together

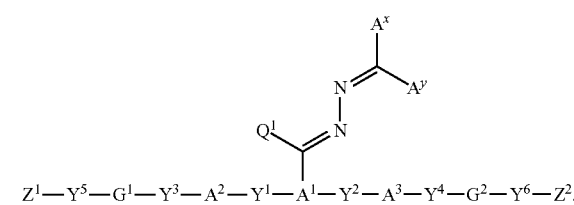

20 Claims, No Drawings

(51) Int. Cl.
*C07D 277/82* (2006.01)
*C07D 209/86* (2006.01)
*C07C 251/88* (2006.01)
*C07D 209/56* (2006.01)
*C08F 24/00* (2006.01)
*C08F 26/06* (2006.01)
*C09K 19/04* (2006.01)
*G02B 5/30* (2006.01)
*C08F 222/10* (2006.01)

(56) References Cited

U.S. PATENT DOCUMENTS

| | | |
|---|---|---|
| 6,203,724 B1 | 3/2001 | Reiffenrath et al. |
| 6,565,974 B1 | 5/2003 | Uchiyama et al. |
| 2002/0159005 A1 | 10/2002 | Arakawa et al. |
| 2003/0102458 A1 | 6/2003 | Nishikawa et al. |
| 2007/0176145 A1 | 8/2007 | Nishikawa et al. |
| 2007/0298191 A1 | 12/2007 | Yamahara et al. |
| 2009/0072194 A1 | 3/2009 | Yamahara et al. |
| 2009/0189120 A1 | 7/2009 | Takeuchi |
| 2010/0201920 A1 | 8/2010 | Adlem et al. |
| 2010/0258764 A1 | 10/2010 | Sakamoto et al. |
| 2010/0301271 A1 | 12/2010 | Adlem et al. |
| 2011/0233464 A1 | 9/2011 | Katoh et al. |
| 2012/0202084 A1 | 8/2012 | Tamura |
| 2014/0200320 A1* | 7/2014 | Sakamoto et al. ............ 526/312 |
| 2014/0235857 A1* | 8/2014 | Sakamoto et al. ............ 544/237 |
| 2015/0175564 A1* | 6/2015 | Sakamoto et al. ............ 526/312 |

FOREIGN PATENT DOCUMENTS

| | | | |
|---|---|---|---|
| JP | 11-52131 A | | 2/1999 |
| JP | 2001-4837 A | | 1/2001 |
| JP | 2002-267838 A | | 9/2002 |
| JP | 2005-208414 A | | 8/2005 |
| JP | 2005-208415 A | | 8/2005 |
| JP | 2005-208416 A | | 8/2005 |
| JP | 2009-149754 A | | 7/2009 |
| JP | 2010-31223 A | | 2/2010 |
| JP | 2010-138283 A | | 6/2010 |
| JP | 2010-159324 A | | 7/2010 |
| JP | 2011-6360 A | | 1/2011 |
| JP | 2011-6361 A | | 1/2011 |
| JP | 2011-207940 A | | 10/2011 |
| JP | 2012136641 A | * | 7/2012 |
| WO | WO 00/26705 A1 | | 5/2000 |
| WO | WO 2011/048989 A1 | | 4/2011 |
| WO | WO 2014061709 A1 | * | 4/2014 |
| WO | WO 2014126113 A1 | * | 8/2014 |

* cited by examiner

POLYMERIZABLE COMPOUND, POLYMERIZABLE COMPOSITION, POLYMER, AND OPTICALLY ANISOTROPIC BODY

TECHNICAL FIELD

The invention relates to a polymerizable compound, a polymerizable composition, and a polymer that can produce an optical film which achieves uniform conversion of polarized light over a wide wavelength band, and also relates to an optically anisotropic article.

BACKGROUND ART

A flat panel display (FPD) that utilizes an optical film (e.g., polarizer and retardation film) can achieve high-resolution display, and has been widely used as a display device (e.g., TV).

Examples of the retardation film include a quarter-wave plate that converts linearly polarized light into circularly polarized light, and a half-wave plate that converts the plane of vibration of linearly polarized light by 90°. Such a retardation film can achieve accurate conversion of specific monochromatic light so that $1/4\lambda$ or $1/2\lambda$ retardation occurs.

However, a known retardation film has a problem in that polarized light that passes through the retardation film is converted into colored polarized light. Specifically, since a material that forms the retardation film has wavelength dispersion with regard to retardation, and a polarization state distribution corresponding to each wavelength occurs for white light that includes different light beams in the visible region, it is impossible to achieve accurate $1/4\lambda$ or $1/2\lambda$ retardation over the entire wavelength band.

In order to solve the above problems, various wideband retardation films that can achieve uniform retardation for light over a wide wavelength band (i.e., retardation films having reverse wavelength dispersion) have been studied (see Patent Documents 1 to 6, for example).

It has been desired to reduce the thickness of the flat panel display as much as possible along with an improvement in performance and widespread use of mobile information terminals (e.g., mobile personal computer and mobile phone) and the like. Therefore, a reduction in thickness of the retardation film has also been desired.

It has been considered that it is most effective to produce a retardation film by applying a polymerizable composition which includes a low-molecular-weight polymerizable compound to a film base in order to reduce the thickness of the retardation film. Various low-molecular-weight polymerizable compounds having excellent wavelength dispersion, and various polymerizable compositions using such polymerizable compounds have been proposed (see Patent Documents 7 to 23, for example).

However, the low-molecular-weight polymerizable compounds or the polymerizable compositions disclosed in Patent Documents 7 to 23 and the like have a number of problems in that reverse wavelength dispersion may be insufficient, or it may be difficult to apply the low-molecular-weight polymerizable compounds or the polymerizable compositions to a film due to a high melting point that is not suitable for an industrial process, or the temperature range in which liquid crystallinity is obtained may be very narrow, or solubility in a solvent generally used for an industrial process may be low. Moreover, since the above low-molecular-weight polymerizable compounds and the like are synthesized by a plurality of steps using a synthesis method that utilizes an expensive reagent, the production cost increases.

RELATED-ART DOCUMENT

Patent Document

Patent Document 1: JP-A-10-68816
Patent Document 2: JP-A-10-90521
Patent Document 3: JP-A-11-52131
Patent Document 4: JP-A-2000-284126 (US20020159005A1)
Patent Document 5: JP-A-2001-4837
Patent Document 6: WO2000/026705
Patent Document 7: JP-A-2002-267838
Patent Document 8: JP-A-2003-160540 (US20030102458A1)
Patent Document 9: JP-A-2005-208414
Patent Document 10: JP-A-2005-208415
Patent Document 11: JP-A-2005-208416
Patent Document 12: JP-A-2005-289980 (US20070176145A1)
Patent Document 13: JP-A-2006-330710 (US20090072194A1)
Patent Document 14: JP-A-2009-179563 (US20090189120A1)
Patent Document 15: JP-A-2010-31223
Patent Document 16: JP-A-2010-537954 (US20100201920A1)
Patent Document 17: JP-T-2010-537955 (US20100301271A1)
Patent Document 18: WO2006/052001 (US20070298191A1)
Patent Document 19: U.S. Pat. No. 6,139,771
Patent Document 20: U.S. Pat. No. 6,203,724
Patent Document 21: U.S. Pat. No. 5,567,349
Patent Document 22: JP-A-2011-6360
Patent Document 23: JP-A-2011-6361

SUMMARY OF THE INVENTION

Technical Problem

The invention was conceived in view of the above situation. An object of the invention is to provide a polymerizable compound, a polymerizable composition, and a polymer that have a practical low melting point, can be produced at low cost, and can produce an optical film that achieves uniform conversion of polarized light over a wide wavelength band, and an optically anisotropic article.

Solution to Problem

The inventors of the invention conducted extensive studies in order to achieve the above object. As a result, the inventors found that an optical film that achieves uniform conversion of polarized light over a wide wavelength band, and shows satisfactory performance can be produced at low cost by utilizing a polymer obtained by polymerizing a polymerizable compound represented by the following formula (I), or a polymerizable composition that includes the polymerizable compound and an initiator.

Several aspects of the invention provide the following polymerizable compound (see (1) to (7)), polymerizable composition (see (8)), polymer (see (9)), and optically anisotropic body (see (10)).

(1) A polymerizable compound represented by the following formula (I),

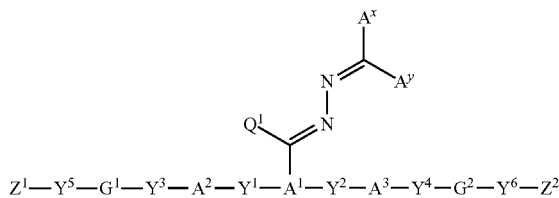

wherein $Y^1$ to $Y^6$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ is a hydrogen atom or an alkyl group having 1 to 6 carbon atoms, $G^1$ and $G^2$ are independently a substituted or unsubstituted divalent aliphatic group having 1 to 20 carbon atoms that may include —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more adjacent —O— or —S— is excluded, $R^2$ is a hydrogen atom or an alkyl group having 1 to 6 carbon atoms, $Z^1$ and $Z^2$ are independently an alkenyl group having 2 to 10 carbon atoms that is substituted with a halogen atom, or unsubstituted, $A^x$ is an organic group having 2 to 30 carbon atoms that includes at least one aromatic ring selected from the group consisting of an aromatic hydrocarbon ring and an aromatic hetero ring, $A^y$ is a hydrogen atom, a substituted or unsubstituted alkyl group having 1 to 6 carbon atoms, or an organic group having 2 to 30 carbon atoms that includes at least one aromatic ring selected from the group consisting of an aromatic hydrocarbon ring and an aromatic hetero ring, provided that the aromatic ring included in $A^x$ and $A^y$ is substituted or unsubstituted, and $A^x$ and $A^y$ optionally bond to each other to form a ring, $A^1$ is a substituted or unsubstituted trivalent aromatic group, $A^2$ and $A^3$ are independently a substituted or unsubstituted divalent aromatic group having 6 to 30 carbon atoms, and $Q^1$ is a hydrogen atom, or a substituted or unsubstituted alkyl group having 1 to 6 carbon atoms.

(2) The polymerizable compound according to (1), wherein the total number of π electrons included in $A^x$ and $A^y$ is 4 to 24.

(3) The polymerizable compound according to (1) or (2), wherein $A^1$ is a substituted or unsubstituted trivalent benzene ring, or a substituted or unsubstituted trivalent naphthalene ring, and $A^2$ and $A^3$ are independently a substituted or unsubstituted phenylene group, or a substituted or unsubstituted naphthylene group.

(4) The polymerizable compound according to any one of (1) to (3), wherein $Y^1$ to $Y^6$ are independently a chemical single bond, —O—, —O—C(=O)—, —C(=O)—O—, or —O—C(=O)—O—.

(5) The polymerizable compound according to any one of (1) to (4), wherein $Z^1$ and $Z^2$ are independently $CH_2$=CH—, $CH_2$=C($CH_3$)—, or $CH_2$=C(Cl)—.

(6) The polymerizable compound according to any one of (1) to (5), wherein $G^1$ and $G^2$ are independently a substituted or unsubstituted divalent aliphatic group having 1 to 12 carbon atoms that may include —O—, —O—C(=O)—, —C(=O)—O—, or —C(=O)—, provided that a case where the aliphatic group includes two or more adjacent —O— is excluded.

(7) The polymerizable compound according to any one of (1) to (5), wherein $G^1$ and $G^2$ are independently a divalent alkylene group having 1 to 12 carbon atoms.

(8) A polymerizable composition including the polymerizable compound according to any one of (1) to (7), and an initiator.

(9) A polymer obtained by polymerizing the polymerizable compound according to any one of (1) to (7), or the polymerizable composition according to (8).

(10) An optically anisotropic article including the polymer according to (9).

Advantageous Effects of the Invention

The polymerizable compound, the polymerizable composition, and the polymer according to the aspects of the invention make it possible to inexpensively obtain an optical film that achieves uniform conversion of polarized light over a wide wavelength band, and shows satisfactory performance.

Since the optically anisotropic article according to the aspect of the invention is produced using the polymer according to the aspect of the invention, it is possible to easily form an optical film that can be obtained at low cost, achieves uniform conversion of polarized light over a wide wavelength band, and shows satisfactory performance. For example, an antireflective film may be produced by combining the optically anisotropic article with a polarizer, and may suitably be used to prevent reflection from a touch panel, an organic electroluminescent device, and the like.

A polymerizable compound, a polymerizable composition, a polymer, and an optically anisotropic article according to the embodiments of the invention are described in detail below.

1) Polymerizable Compound

A polymerizable compound according to one embodiment of the invention is a compound represented by the formula (I).

In the formula (I), $Y^1$ to $Y^6$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—.

$R^1$ is a hydrogen atom or an alkyl group having 1 to 6 carbon atoms.

Examples of the alkyl group having 1 to 6 carbon atoms represented by $R^1$ include a methyl group, an ethyl group, an n-propyl group, an isopropyl group, an n-butyl group, a sec-butyl group, a t-butyl group, an n-pentyl group, an n-hexyl group, and the like.

$R^1$ is preferably a hydrogen atom or an alkyl group having 1 to 4 carbon atoms.

It is preferable that $Y^1$ to $Y^6$ are independently a chemical single bond, —O—, —O—C(=O)—, —C(=O)—O—, or —O—C(=O)—O—.

$G^1$ and $G^2$ are independently a substituted or unsubstituted divalent aliphatic group having 1 to 20 carbon atoms.

Examples of the divalent aliphatic group having 1 to 20 carbon atoms include aliphatic groups having a chain-like structure; aliphatic groups having an alicyclic structure such as a saturated cyclic hydrocarbon (cycloalkane) structure or an unsaturated cyclic hydrocarbon (cycloolefin) structure; and the like.

Examples of a substituent that may substitute the divalent aliphatic group having 1 to 20 carbon atoms include halogen atoms such as a fluorine atom, a chlorine atom, a bromine atom, and an iodine atom; alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

Note that the aliphatic group may include —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more adjacent —O— or —S— is excluded. Among these, —O—, —O—C(=O)—, —C(=O)—O—, and —C(=O)— are preferable.

R$^2$ is a hydrogen atom or an alkyl group having 1 to 6 carbon atoms similar to that represented by R$^1$, and is preferably a hydrogen atom or a methyl group.

Specific examples of the aliphatic group that includes the above group include —CH$_2$—CH$_2$—O—CH$_2$—CH$_2$—, —CH$_2$—CH$_2$—S—CH$_2$—CH$_2$—, —CH$_2$—CH$_2$—O—C(=O)—CH$_2$—CH$_2$—, —CH$_2$—CH$_2$—C(=O)—O—CH$_2$—CH$_2$—, —CH$_2$—CH$_2$—C(=O)—O—CH$_2$—, —CH$_2$—O—C(=O)—O—CH$_2$—CH$_2$—, —CH$_2$—CH$_2$—NR$^2$—C(=O)—CH$_2$—CH$_2$—, —CH$_2$—CH$_2$—C(=O)—NR$^2$—CH$_2$—, —CH$_2$—NR$^2$—CH$_2$—CH$_2$—, —CH$_2$—C(=O)—CH$_2$—, and the like.

It is preferable that G$^1$ and G$^2$ are independently an aliphatic group having a chain-like structure (e.g., an alkylene group having 1 to 20 carbon atoms or an alkenylene group having 2 to 20 carbon atoms), more preferably an alkylene group having 1 to 12 carbon atoms (e.g., methylene group, ethylene group, trimethylene group, propylene group, tetramethylene group, pentamethylene group, hexamethylene group, or octamethylene group), and particularly preferably a tetramethylene group (—(CH$_2$)$_4$—) or a hexamethylene group (—(CH$_2$)$_6$—), in order to ensure that the intended effects of the invention can be more advantageously achieved.

Z$^1$ and Z$^2$ are independently an alkenyl group having 2 to 10 carbon atoms that is substituted with a halogen atom, or unsubstituted.

The number of carbon atoms of the alkenyl group is preferably 2 to 6. Examples of the halogen atom that may substitute the alkenyl group represented by Z$^1$ and Z$^2$ include a fluorine atom, a chlorine atom, a bromine atom, and the like. Among these, a chlorine atom is preferable.

Specific examples of the alkenyl group having 2 to 10 carbon atoms represented by Z$^1$ and Z$^2$ include CH$_2$=CH—, CH$_2$=C(CH$_3$)—, CH$_2$=CH—CH$_2$—, CH$_3$—CH=CH—, CH$_2$=CH—CH$_2$—CH$_2$—, CH$_2$=C(CH$_3$)—CH$_2$—CH$_2$—, (CH$_3$)$_2$C=CH—CH$_2$—, (CH$_3$)$_2$C=CH—CH$_2$—CH$_2$—, CH$_2$=C(Cl)—, CH$_2$=C(CH$_3$)—CH$_2$—, CH$_3$—CH=CH—CH$_2$—, and the like.

It is preferable that Z$^1$ and Z$^2$ are independently CH$_2$=CH—, CH$_2$=C(CH$_3$)—, CH$_2$=C(Cl)—, CH$_2$=CH—CH$_2$—, CH$_2$=C(CH$_3$)—CH$_2$—, or CH$_2$=C(CH$_3$)—CH$_2$—CH$_2$—, more preferably CH$_2$=CH—, CH$_2$=C(CH$_3$)—, or CH$_2$=C(Cl)—, and still more preferably CH$_2$=CH—, in order to ensure that the intended effects of the invention can be more advantageously achieved.

A$^x$ is an organic group having 2 to 30 carbon atoms that includes at least one aromatic ring selected from the group consisting of an aromatic hydrocarbon ring and an aromatic hetero ring.

The term "aromatic ring" used herein refers to a cyclic structure that exhibits aromaticity according to Huckel's rule in a broad sense (i.e., a cyclic conjugated structure that includes (4n+2) π electrons, and a structure that exhibits aromaticity in which lone pairs of heteroatoms such as sulfur or oxygen are involved in the π electron system (e.g., thiophene and furan)).

The organic group having 2 to 30 carbon atoms represented by A$^x$ that includes at least one aromatic ring selected from the group consisting of an aromatic hydrocarbon ring and an aromatic hetero ring, may include a plurality of aromatic rings, and may include an aromatic hydrocarbon ring and an aromatic hetero ring.

Examples of the aromatic hydrocarbon ring include a benzene ring, a naphthalene ring, an anthracene ring, a fluorene ring, and the like. Examples of the aromatic hetero ring include 5-membered aromatic hetero rings such as a pyrrole ring, a furan ring, a thiophene ring, a pyrazole ring, an imidazole ring, an oxazole ring, and a thiazole ring; 6-membered aromatic hetero rings such as a pyridine ring, a pyridazine ring, a pyrimidine ring, and a pyrazine ring; fused aromatic hetero rings such as a benzimidazole ring, a benzothiophene ring, a benzoxazole ring, a benzothiazole ring, and a carbazole ring; and the like.

The aromatic ring included in A$^x$ may be substituted with a substituent at an arbitrary position. Examples of the substituent include halogen atoms such as a fluorine atom and a chlorine atom; a cyano group; alkyl groups having 1 to 6 carbon atoms such as a methyl group, an ethyl group, and a propyl group; alkenyl groups having 2 to 6 carbon atoms such as a vinyl group and an allyl group; alkyl halide groups having 1 to 6 carbon atoms such as a trifluoromethyl group; substituted amino groups; alkoxy groups having 1 to 6 carbon atoms such as a methoxy group, an ethoxy group, and an isopropoxy group; a nitro group; aryl groups such as a phenyl group and a naphthyl group; a —C(=O)—OR group; an —SO$_2$R group; and the like. Note that R is an alkyl group having 1 to 6 carbon atoms or an aryl group having 6 to 14 carbon atoms.

The aromatic ring included in A$^x$ may be substituted with a plurality of identical or different substituents, and two adjacent substituents may bond to each other to form a ring. The ring formed by two adjacent substituents may be a monocyclic ring, or may be a fused polycyclic ring.

Note that the number of carbon atoms (i.e., 2 to 3) of the organic group represented by A$^x$ refers to the total number of carbon atoms of the organic group excluding the number of carbon atoms of a substituent. This also applies to the number of carbon atoms of the organic group represented by A$^y$.

Examples of the organic group having 2 to 30 carbon atoms represented by A$^x$ that includes at least one aromatic ring selected from the group consisting of an aromatic hydrocarbon ring and an aromatic hetero ring include aromatic cyclic hydrocarbon groups; aromatic heterocyclic groups; alkyl group having 3 to 30 carbon atoms that include at least one aromatic ring selected from the group consisting of an aromatic hydrocarbon ring and an aromatic hetero ring; alkenyl groups having 4 to 30 carbon atoms that include at least one aromatic ring selected from the group consisting of an aromatic hydrocarbon ring and an aromatic hetero ring; alkynyl groups having 4 to 30 carbon atoms that include at least one aromatic ring selected from the group consisting of an aromatic hydrocarbon ring and an aromatic hetero ring; and the like.

A$^y$ is a hydrogen atom, a substituted or unsubstituted alkyl group having 1 to 6 carbon atoms, or an organic group having 2 to 30 carbon atoms that includes at least one aromatic ring selected from the group consisting of an aromatic hydrocarbon ring and an aromatic hetero ring.

Examples of the substituted or unsubstituted alkyl group having 1 to 6 carbon atoms represented by A$^y$ include a methyl group, an ethyl group, an n-propyl group, an isopropyl group, an n-butyl group, a sec-butyl group, a t-butyl group, an n-pentyl group, an n-hexyl group, and the like.

Examples of a substituent that may substitute the substituted or unsubstituted alkyl group having 1 to 6 carbon atoms include halogen atoms such as a fluorine atom and a chlorine atom; a cyano group; substituted amino groups such as a dimethylamino group; alkoxy groups having 1 to 6 carbon atoms such as a methoxy group, an ethoxy group, and an isopropoxy group; a nitro group; aryl groups such as a phenyl group and a naphthyl group; a —C(=O)—OR group; an —SO$_2$R group; and the like. Note that R is the same as defined above.

Examples of the organic group having 2 to 30 carbon atoms represented by A$^y$ that includes at least one aromatic ring selected from the group consisting of an aromatic hydrocarbon ring and an aromatic hetero ring, include those mentioned above in connection with A$^x$.

Specific examples of the organic group having 2 to 30 carbon atoms represented by A$^x$ and A$^y$ that includes at least one aromatic ring selected from the group consisting of an aromatic hydrocarbon ring and an aromatic hetero ring, are shown below. Note that the organic group is not limited to the following groups. "–" in the following formulas is a bonding hand of the aromatic ring (hereinafter the same).

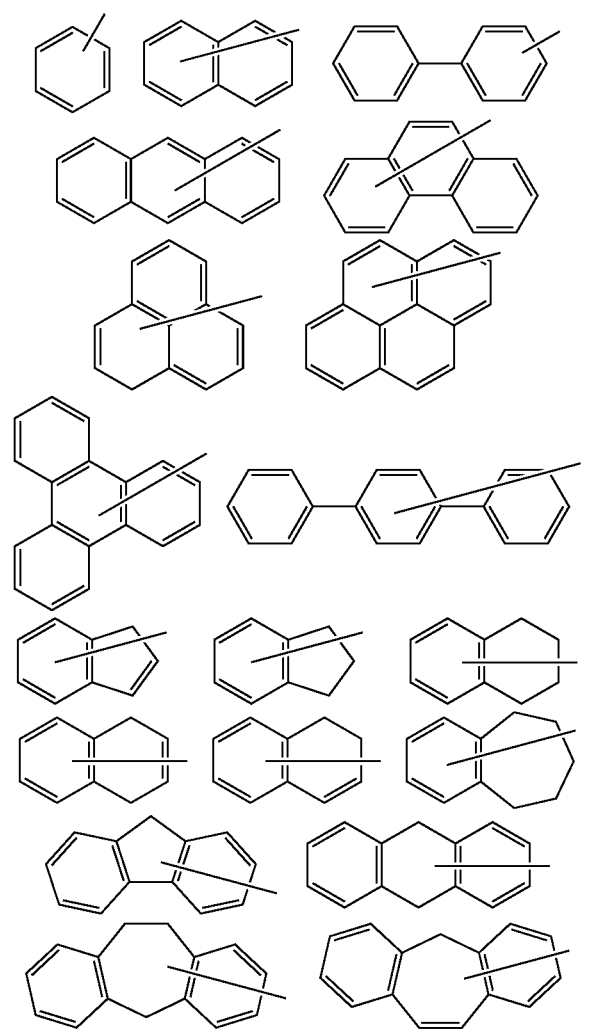

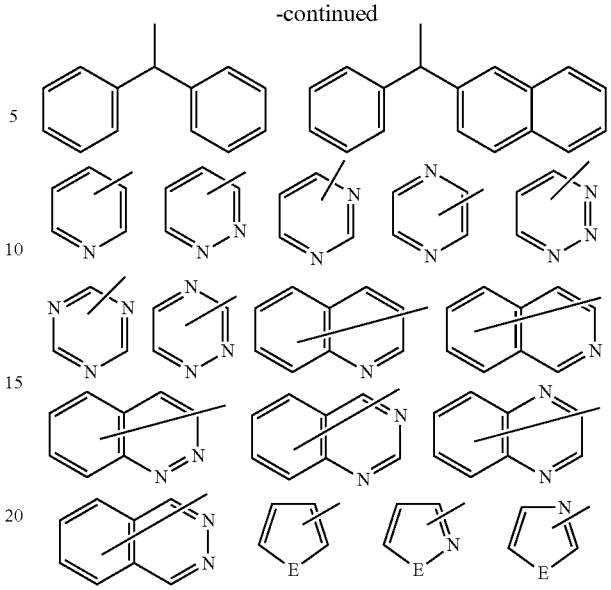

wherein E is NR$^3$, an oxygen atom, or a sulfur atom, and R$^3$ is a hydrogen atom, or an alkyl group having 1 to 6 carbon atoms (e.g., methyl group or ethyl group).

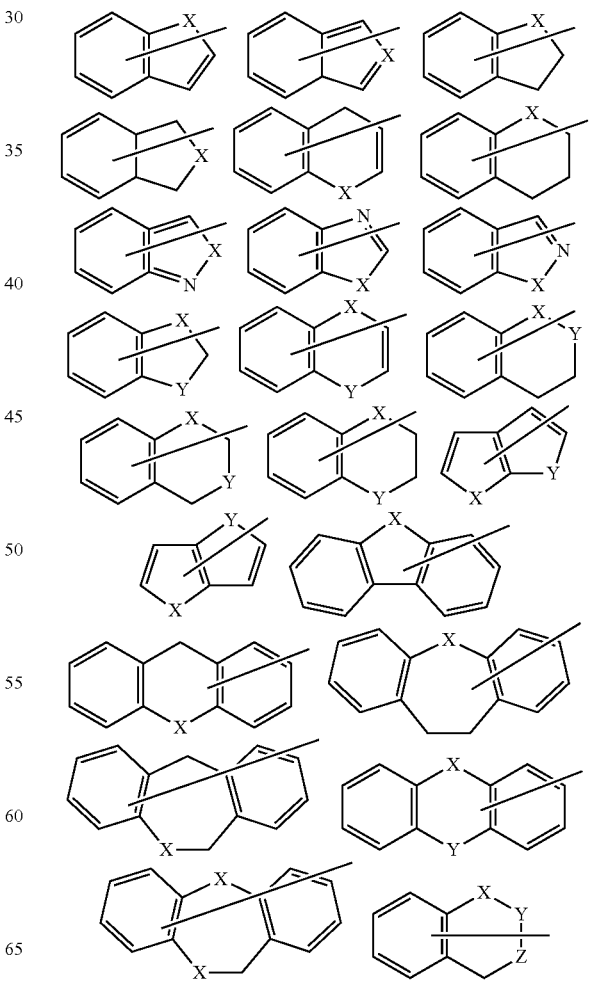

-continued

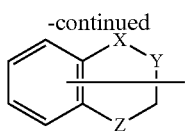

wherein X, Y, and Z are independently $NR^3$, an oxygen atom, a sulfur atom, —SO—, or —$SO_2$—, provided that a case where two or more oxygen atoms, sulfur atoms, —SO—, or —$SO_2$— are situated at adjacent positions is excluded, and $R^3$ is the same as defined above.

Among these, the following groups are preferable.

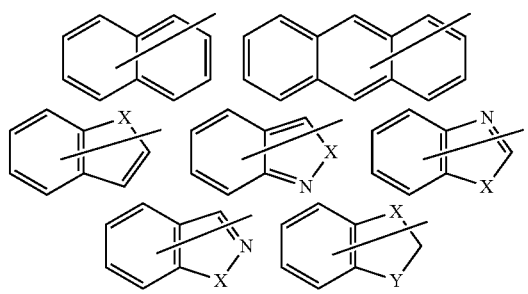

Among these, the following groups are particularly preferable.

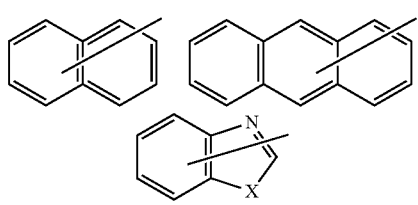

$A^x$ and $A^y$ optionally bond to each other to form a ring. In this case, it is preferable that $A^x$ and $A^y$ bond to each other to form a substituted or unsubstituted unsaturated hetero ring having 4 to 30 carbon atoms, or a substituted or unsubstituted unsaturated carbon ring having 6 to 30 carbon atoms.

The unsaturated hetero ring having 4 to 30 carbon atoms and the unsaturated carbon ring having 6 to 30 carbon atoms are not particularly limited, and may or may not exhibit aromaticity. The following rings are preferable as the unsaturated hetero ring having 4 to 30 carbon atoms and the unsaturated carbon ring having 6 to 30 carbon atoms. Note that a double bond that connects the ring and the nitrogen atom is also shown in the following formulas for convenience (hereinafter the same).

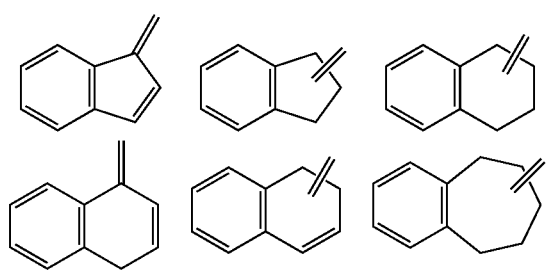

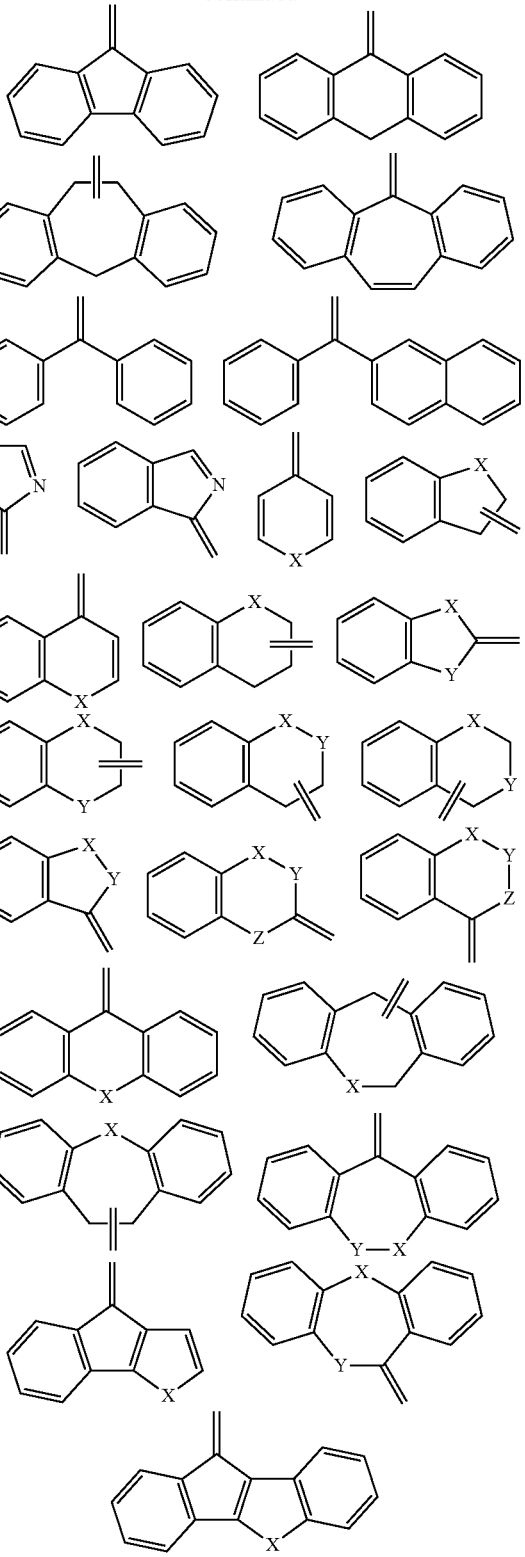

wherein X, Y, and Z are the same as defined above.

The above rings may be substituted with a substituent.

Examples of the substituent include halogen atoms, a cyano group, alkyl groups having 1 to 6 carbon atoms, alkoxy groups having 1 to 6 carbon atoms, a nitro group, a —C(=O)—OR group, an —SO$_2$R group, and the like. Note that R is the same as defined above.

It is particularly preferable that $A^x$ and $A^y$ bond to each other to form any of the following rings.

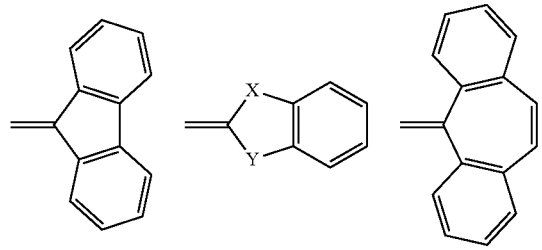

wherein X and Y are the same as defined above. It is preferable that X and Y are a sulfur atom and NR$^3$ (wherein R$^3$ is the same as defined above), respectively.

The total number of π electrons included in $A^x$ and $A^y$ is preferably 4 to 24 in order to ensure that the intended effects of the invention can be more advantageously achieved.

It is preferable that $A^x$ is an aromatic group having 4 to 30 carbon atoms, and $A^y$ is a hydrogen atom or a substituted or unsubstituted alkyl group, or $A^x$ and $A^y$ bond to each other to form an unsaturated hetero ring or an unsaturated carbon ring. It is more preferable that $A^x$ is a group having any of the following structures, and $A^y$ is a hydrogen atom or a substituted or unsubstituted alkyl group,

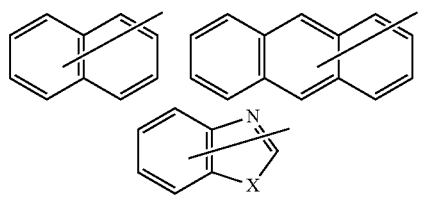

wherein X is the same as defined above, or
$A^x$ and $A^y$ bond to each other to form a ring represented by any of the following formulas.

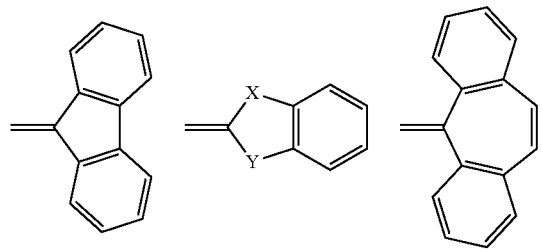

wherein X and Y are the same as defined above.

$A^1$ is a substituted or unsubstituted trivalent aromatic group. The trivalent aromatic group may be a trivalent carbocyclic aromatic group, or may be a trivalent heterocyclic aromatic group. It is preferable that the trivalent aromatic group is a trivalent carbocyclic aromatic group, and more preferably a trivalent benzene ring group or a trivalent naphthalene ring group represented by the following formulas. Note that the substituents $Y^1$ and $Y^2$ are also shown in the following formulas so that the bonding state can be easily understood ($Y^1$ and $Y^2$ are the same as defined above; hereinafter the same).

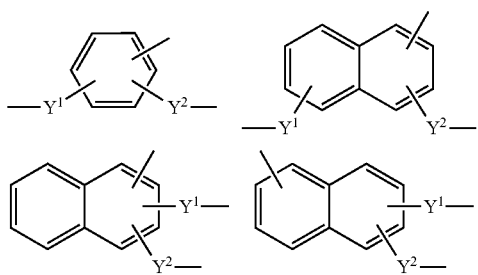

$A^1$ is more preferably any of the groups represented by the following formulas (A11) to (A18), and particularly preferably the group represented by the formula (A11).

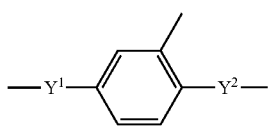
(A11)

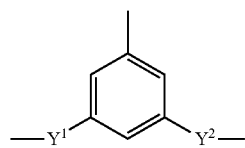
(A12)

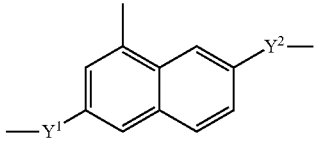
(A13)

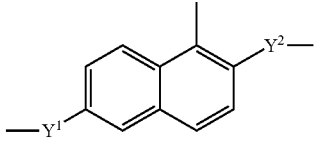
(A14)

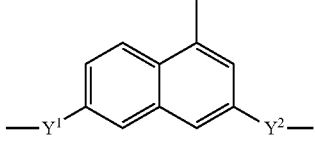
(A15)

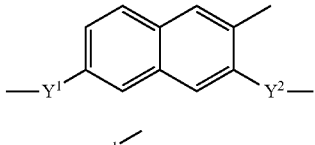
(A16)

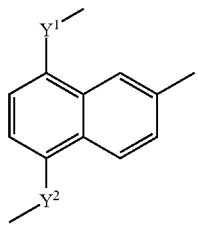
(A17)

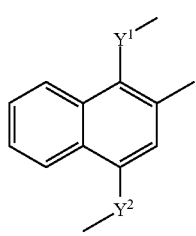

(A18)

Examples of a substituent that may substitute the trivalent aromatic group represented by $A^1$ include those mentioned above in connection with a substituent that may substitute the aromatic ring included in $A^X$. It is preferable that $A^1$ is unsubstituted.

$A^2$ and $A^3$ are independently a substituted or unsubstituted divalent aromatic group having 6 to 30 carbon atoms.

The aromatic group represented by $A^2$ and $A^3$ may be a monocyclic aromatic group, or may be a polycyclic aromatic group.

Specific examples of the aromatic group represented by $A^2$ and $A^3$ include the following groups.

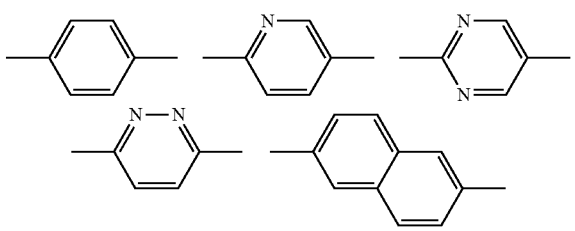

The aromatic group represented by $A^2$ and $A^3$ may be substituted with a substituent at an arbitrary position. Examples of the substituent include halogen atoms, a cyano group, a hydroxyl group, alkyl groups having 1 to 6 carbon atoms, alkoxy groups having 1 to 6 carbon atoms, a nitro group, a —C(=O)—OR group, and the like. Note that R is an alkyl group having 1 to 6 carbon atoms. Among these, halogen atoms, alkyl groups, and alkoxy groups are preferable. A fluorine atom is preferable as the halogen atom. A methyl group, an ethyl group, and a propyl group are preferable as the alkyl group. A methoxy group and an ethoxy group are preferable as the alkoxy group.

It is preferable that $A^2$ and $A^3$ are independently the group represented by the following formula (A21) or (A22) that may be substituted with a substituent, and more preferably the group represented by the formula (A21) that may be substituted with a substituent.

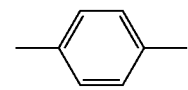

(A21)

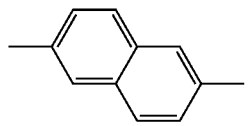

(A22)

$Q^1$ is a hydrogen atom, or a substituted or unsubstituted alkyl group having 1 to 6 carbon atoms.

Examples of the substituted or unsubstituted alkyl group having 1 to 6 carbon atoms include those mentioned above in connection with $A^x$.

$Q^1$ is preferably a hydrogen atom or an alkyl group having 1 to 6 carbon atoms, and more preferably a hydrogen atom.

The polymerizable compound according to one embodiment of the invention may be produced by the following production method 1 or 2, for example.

Production Method 1

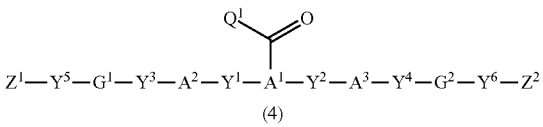

wherein $Y^1$ to $Y^6$, $G^1$, $G^2$, $Z^1$, $Z^2$, $A^x$, $A^y$, $A^1$ to $A^3$, and $Q^1$ are the same as defined above.

Specifically, the hydrazone compound represented by the formula (3) (hydrazone compound (3)) is reacted with the carbonyl compound represented by the formula (4) (carbonyl compound (4)) in a molar ratio (hydrazone compound (3): carbonyl compound (4)) of 1:2 to 2:1 (preferably 1:1.5 to 1.5:1) to produce the polymerizable compound represented by the formula (I) with high selectivity in high yield.

The above reaction may be effected in the presence of an acid catalyst such as an organic acid (e.g., (±)-10-camphorsulfonic acid or p-toluenesulfonic acid) or an inorganic acid (e.g., hydrochloric acid or sulfuric acid). The reaction time may be shortened, and the yield may be improved as a result of adding the acid catalyst. The acid catalyst is normally added in an amount of 0.001 to 1 mol based on 1 mol of the carbonyl compound (4). The acid catalyst may be added directly, or may be added in the form of a solution prepared by dissolving the acid catalyst in an appropriate solvent.

The solvent is not particularly limited as long as the solvent is inert to the reaction. Examples of the solvent include alcohol-based solvents such as methyl alcohol, ethyl alcohol, n-propyl alcohol, isopropyl alcohol, n-butyl alcohol, isobutyl alcohol, sec-butyl alcohol, tert-butyl alcohol, n-pentyl alcohol, and amyl alcohol; ether-based solvents such as diethyl ether, tetrahydrofuran, 1,2-dimethoxyethane, 1,4-dioxane, and cyclopentyl methyl ether; ester-based solvents such as ethyl acetate, propyl acetate, and methyl propionate; aromatic hydrocarbon-based solvents such as benzene, toluene, and xylene; aliphatic hydrocarbon-based solvents such as n-pentane, n-hexane, and n-heptane; amide-based solvents such as N,N-dimethylformamide, N-methylpyrrolidone, and hexamethylphosphoric triamide; sulfur-containing solvents such as dimethyl sulfoxide and sulfolane; mixed solvents including two or more solvents among these solvents; and the like.

Among these, alcohol-based solvents, ether-based solvents, and mixed solvents of an alcohol-based solvent and an ether-based solvent are preferable.

The solvent may be used in an appropriate amount taking account of the type of each compound, the reaction scale, and the like. The solvent is normally used in an amount of 1 to 100 g per gram of the hydrazone compound (3).

The reaction proceeds smoothly when the reaction temperature is within the range from −10° C. to the boiling point of the solvent. The reaction time is determined taking account of the reaction scale, and is normally several minutes to several hours.

Production Method 2

The polymerizable compound represented by the formula (I) wherein the group represented by $Z^2$-$Y^6$-$G^2$-$Y^4$-$A^3$-$Y^2$- is identical with the group represented by $Z^1$-$Y^5$-$G^1$-$Y^3$-$A^2$-$Y^1$-, and $Y^1$ is a group represented by $Y^{11}$—C(=O)—O— (hereinafter referred to as "compound (I')") may be produced by the following steps 1 and 2.

(Step 1)

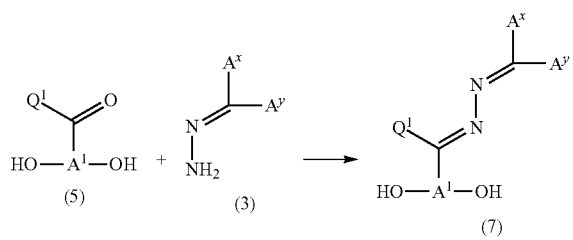

(Step 2)

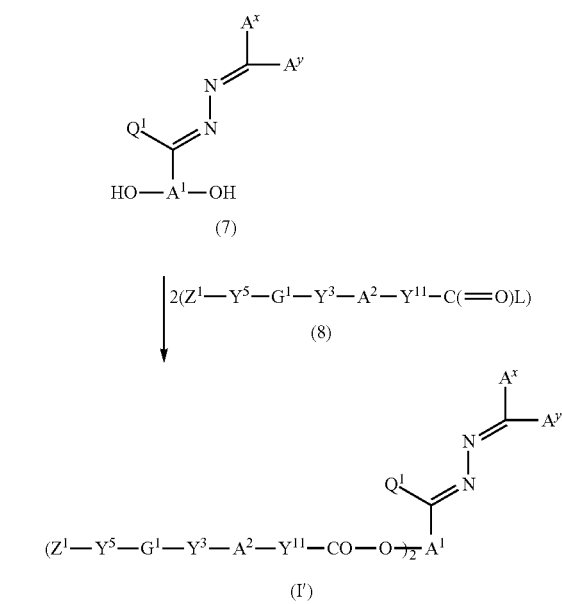

wherein $Y^3$, $Y^5$, $G^1$, $Z^1$, $A^x$, $A^y$, $A^1$, $A^2$, and $Q^1$ are the same as defined above, $Y^{11}$ is a group whereby $Y^1$ is $Y^{11}$—C(=O)—O—, $Y^1$ is the same as defined above, and L is a leaving group (e.g., hydroxyl group, halogen atom, methanesulfonyloxy group, or p-toluenesulfonyloxy group).

Specifically, the dihydroxy compound that includes a group represented by —C(=O)-$Q^1$ (wherein $Q^1$ is the same as defined above) (dihydroxy compound (5)) is reacted with the hydrazone compound (3) to obtain the hydroxy compound (7) (step 1), and the hydroxy compound (7) is reacted with the compound represented by the formula (8) (compound (8)) in an amount equal to or more than the 2-fold equivalent (step 2) to produce the compound represented by the formula (I').

In the step 1, the dihydroxy compound (5) is reacted with the hydrazone compound (3) in a solvent in a molar ratio (dihydroxy compound (5):hydrazone compound (3)) of 1:1 to 1:5 (preferably 1:1 to 1:3) to obtain the hydroxy compound (7).

The solvent used in the step 1 is not particularly limited as long as the solvent is inert to the reaction.

Examples of the solvent include those mentioned above in connection with the production method 1. The solvent may be used in an appropriate amount taking account of the type of each compound, the reaction scale, and the like. The solvent is normally used in an amount of 1 to 100 g per gram of the hydrazone compound (3).

In the step 2, the hydroxy compound (7) that has been optionally purified is reacted with the compound (8) in a molar ratio (hydroxy compound (7):compound (8)) of 1:2 to 1:4 (preferably 1:2 to 1:3) to produce the compound (I') with high selectivity in high yield.

When the compound (8) is a compound (carboxylic acid) represented by the formula (8) wherein L is a hydroxyl group, the target product may be obtained by effecting the reaction in the presence of a dehydration-condensation agent (e.g., 1-ethyl-3-(3-dimethylaminopropyl)carbodiimide hydrochloride or dicyclohexylcarbodiimide).

The dehydration-condensation agent is normally used in an amount of 1 to 3 mol based on 1 mol of the compound (8).

When the compound (8) is a compound (acid halide) represented by the formula (8) wherein L is a halogen atom, the target product may be obtained by effecting the reaction in the presence of a base.

Examples of the base include organic bases such as triethylamine and pyridine, and inorganic bases such as sodium hydroxide, sodium carbonate, and sodium hydrogen carbonate.

The base is normally used in an amount of 1 to 3 mol based on 1 mol of the compound (8).

When the compound (8) is a compound (mixed acid anhydride) represented by the formula (8) wherein L is a methanesulfonyloxy group or a p-toluenesulfonyloxy group, the target product may be obtained in the same manner as in the case where L is a halogen atom.

Examples of the solvent used in the step 2 include chlorine-based solvents such as chloroform and methylene chloride; amide-based solvents such as N-methylpyrrolidone, N,N-dimethylformamide, N,N-dimethylacetamide, and hexamethylphosphoric triamide; ether-based solvents such as 1,4-dioxane, cyclopentyl methyl ether, tetrahydrofuran, tetrahydropyran, 1,2-dimethoxyethane; sulfur-containing solvents such as dimethyl sulfoxide and sulfolane; aromatic hydrocarbon-based solvents such as benzene, toluene, and xylene; aliphatic hydrocarbon-based solvents such as n-pentane, n-hexane, and n-octane; alicyclic hydrocarbon-based solvents such as cyclopentane and cyclohexane; mixed solvents including two or more solvents among these solvents; and the like.

The solvent may be used in an appropriate amount taking account of the type of each compound, the reaction scale, and the like. The solvent is normally used in an amount of 1 to 50 g per gram of the hydroxy compound (7).

The hydrazone compound (3) may be produced as described below.

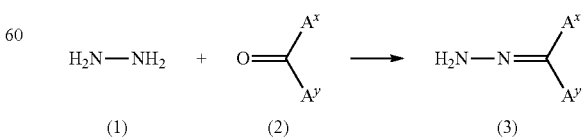

Specifically the carbonyl compound represented by the formula (2) is reacted with hydrazine (1) in an appropriate solvent in a molar ratio (carbonyl compound (2):hydrazine (1)) of 1:1 to 1:20 (preferably 1:2 to 1:10) to obtain the corresponding hydrazone compound (3).

Hydrazine monohydrate is normally used as hydrazine. Commercially available hydrazine may be used directly.

The solvent used for the above reaction is not particularly limited as long as the solvent is inert to the reaction. Examples of the solvent include alcohol-based solvents such as methyl alcohol, ethyl alcohol, n-propyl alcohol, isopropyl alcohol, n-butyl alcohol, isobutyl alcohol, sec-butyl alcohol, tert-butyl alcohol, n-pentyl alcohol, and amyl alcohol; ether-based solvents such as diethyl ether, tetrahydrofuran, 1,2-dimethoxyethane, 1,4-dioxane, and cyclopentyl methyl ether; aromatic hydrocarbon-based solvents such as benzene, toluene, and xylene; aliphatic hydrocarbon-based solvents such as n-pentane, n-hexane, and n-heptane; amide-based solvents such as N,N-dimethylformamide, N-methylpyrrolidone, and hexamethylphosphoric triamide; sulfur-containing solvents such as dimethyl sulfoxide and sulfolane; mixed solvents of two or more of these solvents; and the like.

Among these, alcohol-based solvents, ether-based solvents, and mixed solvents of an alcohol-based solvent and an ether-based solvent are preferable.

The solvent may be used in an appropriate amount taking account of the type of each compound, the reaction scale, and the like. The solvent is normally used in an amount of 1 to 100 g per gram of hydrazine.

The reaction proceeds smoothly when the reaction temperature is within the range from −10° C. to the boiling point of the solvent. The reaction time is determined taking account of the reaction scale, and is normally several minutes to several hours.

The hydroxy compound (7) may also be obtained by the following method.

(Step 1a)

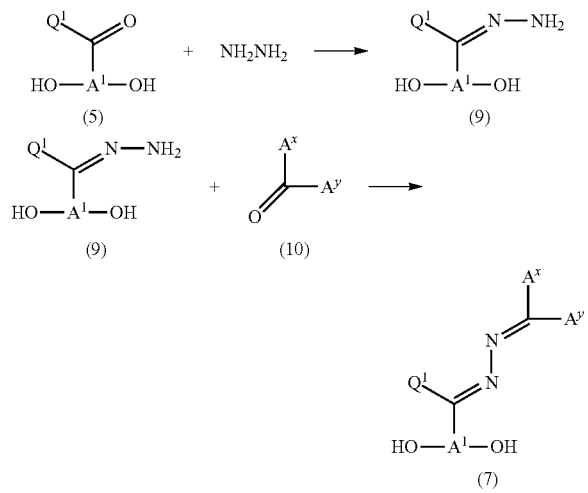

Specifically, hydrazine is reacted with the dihydroxy compound (5) to obtain the hydrazone compound represented by the formula (9), and the hydrazone compound is reacted with the carbonyl compound represented by the formula (10) to obtain the hydroxy compound (7).

The carbonyl compound (4) and the compound (8) may be produced by appropriately bonding and modifying a plurality of known compounds having a desired structure by arbitrarily combining an ether linkage (—O—)-forming reaction, an ester linkage (—C(=O)—O— or —O—C(=O)—)-forming reaction, a carbonate linkage (—O—C(=O)—O—)-forming reaction, and an amide linkage (—C(=O)NH— or —NHC(=O)—)-forming reaction.

An ether linkage may be formed as described below, for example.

(i) A compound represented by D1-hal (wherein Hal is a halogen atom; hereinafter the same) and a compound represented by D2-OMet (wherein Met is an alkali metal (mainly sodium; hereinafter the same) are mixed and condensed (Williamson synthesis). Note that D1 and D2 are an arbitrary organic group (hereinafter the same).

(ii) A compound represented by D1-hal and a compound represented by D2-OH are mixed and condensed in the presence of a base (e.g., sodium hydroxide or potassium hydroxide).

(iii) A compound represented by D1-Epo (wherein Epo is an epoxy group) and a compound represented by D2-OH are mixed and condensed in the presence of a base (e.g., sodium hydroxide or potassium hydroxide).

(iv) A compound represented by D1-OFN (wherein OFN is a group that includes an unsaturated bond) and a compound represented by D2-OMet are mixed and subjected to an addition reaction in the presence of a base (e.g., sodium hydroxide or potassium hydroxide).

(v) A compound represented by D1-hal and a compound represented by D2-OMet are mixed and condensed in the presence of copper or cuprous chloride (Ullmann condensation).

An ester linkage and an amide linkage may be formed as described below, for example.

(vi) A compound represented by D1-COOH and a compound represented by D2-OH or D2-NH$_2$ are subjected to dehydration and condensation in the presence of a dehydration-condensation agent (e.g., N,N-dicyclohexylcarbodiimide).

(vii) A compound represented by D1-COOH is reacted with a halogenating agent to obtain a compound represented by D1-CO-hal, and the compound represented by D1-CO-hal is reacted with a compound represented by D2-OH or D2-NH$_2$ in the presence of a base.

(viii) A compound represented by D1-COOH is reacted with an acid anhydride to obtain a mixed acid anhydride, and the mixed acid anhydride is reacted with a compound represented by D2-OH or D2-NH$_2$.

(ix) A compound represented by D1-COOH and a compound represented by D2-OH or D2-NH$_2$ are subjected to dehydration and condensation in the presence of an acid catalyst or a base catalyst.

The target product may be isolated by performing a post-treatment operation normally employed in organic chemistry after completion of the reaction, optionally followed by a known purification/separation means such as column chromatography, recrystallization, or distillation.

The structure of the target product may be identified by measurement (e.g., NMR spectrometry, IR spectrometry, or mass spectrometry), elementary analysis, or the like.

2) Polymerizable Composition

A polymerizable composition according to one embodiment of the invention includes the polymerizable compound according to one embodiment of the invention, and an initiator. The initiator is used to ensure that the polymerizable composition according to one embodiment of the invention is more efficiently polymerized.

The initiator may be appropriately selected depending on the type of the polymerizable group included in the polymerizable compound. For example, a radical initiator may be used when the polymerizable group is a radically polymerizable group. An anionic initiator may be used when the polymerizable group is an anionically polymerizable group. A cationic initiator may be used when the polymerizable group is a cationically polymerizable group. A thermal radical generator or a photo-radical generator may be used as the radical initiator. It is preferable to use a photo-radical generator.

Examples of the photo-radical generator include acetophenone-based compounds, biimidazole-based compounds, triazine-based compounds, O-acyloxime-based compounds, onium salt-based compounds, benzoin-based compounds, benzophenone-based compounds, α-diketone-based compounds, polynuclear quinone-based compounds, xanthone-based compounds, diazo-based compounds, imide sulfonate-based compounds, and the like. These compounds generate active radicals and/or an active acid upon exposure. These photo-radical generators may be used either alone or in combination.

Specific examples of the acetophenone-based compounds include 2-hydroxy-2-methyl-1-phenylpropan-1-one, 2-methyl-1-[4-(methylthio)phenyl]-2-morpholinopropan-1-one, 2-benzyl-2-dimethylamino-1-(4-morpholinophenyl)butan-1-one, 1-hydroxycyclohexyl phenyl ketone, 2,2-dimethoxy-1,2-diphenylethan-1-one, 1,2-octanedione, 2-benzyl-2-dimethylamino-4'-morpholinobutyrophenone, and the like.

Specific examples of the biimidazole-based compounds include 2,2'-bis(2-chlorophenyl)-4,4',5,5'-tetrakis(4-ethoxycarbonylphenyl)-1,2'-biimidazole, 2,2'-bis(2-bromophenyl)-4,4',5,5'-tetrakis(4-ethoxycarbonylphenyl)-1,2'-biimidazole, 2,2'-bis(2-chlorophenyl)-4,4',5,5'-tetraphenyl-1,2'-biimidazole, 2,2'-bis(2,4-dichlorophenyl)-4,4',5,5'-tetraphenyl-1,2'-biimidazole, 2,2'-bis(2,4,6-trichlorophenyl)-4,4',5,5'-tetraphenyl-1,2'-biimidazole, 2,2'-bis(2-bromophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-tribromophenyl)-4,4',5,5'-tetraphenyl-1,2'-biimidazole, and the like.

When using a biimidazole-based compound as a photoinitiator, it is preferable to use a hydrogen donor in combination with the biimidazole-based compound since sensitivity can be further improved.

The term "hydrogen donor" used herein refers to a compound that can donate a hydrogen atom to radicals generated by the biimidazole-based compound upon exposure. A mercaptan-based compound, an amine-based compound, and the like are preferable as the hydrogen donor.

Examples of the mercaptan-based compound include 2-mercaptobenzothiazole, 2-mercaptobenzoxazole, 2-mercaptobenzimidazole, 2,5-dimercapto-1,3,4-thiadiazole, 2-mercapto-2,5-dimethylaminopyridine, and the like.

Examples of the amine-based compound include 4,4'-bis(dimethylamino)benzophenone, 4,4'-bis(diethylamino)benzophenone, 4-diethylaminoacetophenone, 4-dimethylaminopropiophenone, ethyl-4-dimethylaminobenzoate, 4-dimethylaminobenzoic acid, 4-dimethylaminobenzonitrile, and the like.

Specific examples of the triazine-based compounds include triazine-based compounds that include a halomethyl group, such as 2,4,6-tris(trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, and 2-(4-n-butoxyphenyl)-4,6-bis(trichloromethyl)-s-triazine.

Specific examples of the O-acyloxime-based compounds include 1-[4-(phenylthio)phenyl]-heptane-1,2-dione-2-(O-benzoyloxime), 1-[4-(phenylthio)phenyl]-octane-1,2-dione-2-(O-benzoyloxime), 1-[4-(benzoyl)phenyl]-octane-1,2-dione-2-(O-benzoyloxime), 1-[9-ethyl-6-(2-methylbenzoyl)-9H-carbazol-3-yl]-ethanone-1-(O-acetyloxime), 1-[9-ethyl-6-(3-methylbenzoyl)-9H-carbazol-3-yl]-ethanone-1-(O-acetyloxime), 1-(9-ethyl-6-benzoyl-9H-carbazol-3-yl)-ethanone-1-(O-acetyloxime), ethanone-1-[9-ethyl-6-(2-methyl-4-tetrahydrofuranylbenzoyl)-9H-carbazol-3-yl]-1-(O-acetyloxime), ethanone-1-[9-ethyl-6-(2-methyl-4-tetrahydropyranylbenzoyl)-9H-carbazol-3-yl]-1-(O-acetyloxime), ethanone-1-[9-ethyl-6-(2-methyl-5-tetrahydrofuranylbenzoyl)-9H-carbazol-3-yl]-1-(O-acetyloxime), ethanone-1-[9-ethyl-6-(2-methyl-5-tetrahydropyranylbenzoyl)-9H-carbazol-3-yl]-1-(O-acetyloxime), ethanone-1-[9-ethyl-6-{2-methyl-4-(2,2-dimethyl-1,3-dioxolanyl)benzoyl}-9H-carbazol-3-yl]-1-(O-acetyloxime), ethanone-1-[9-ethyl-6-(2-methyl-4-tetrahydrofuranylmethoxybenzoyl)-9H-carbazol-3-yl]-1-(O-acetyloxime), ethanone-1-[9-ethyl-6-(2-methyl-4-tetrahydropyranylmethoxybenzoyl)-9H-carbazol-3-yl]-1-(O-acetyloxime), ethanone-1-[9-ethyl-6-(2-methyl-5-tetrahydrofuranylmethoxybenzoyl)-9H-carbazol-3-yl]-1-(O-acetyloxime), ethanone-1-[9-ethyl-6-(2-methylbenzoyl)-9H-carbazol-3-yl]-1-(O-acetyloxime), ethanone-1-[9-ethyl-6-(2-methyl-5-tetrahydropyranylmethoxybenzoyl)-9H-carbazol-3-yl]-1-(O-acetyloxime), ethanone-1-[9-ethyl-6-{2-methyl-4-(2,2-dimethyl-1,3-dioxolanyl)methoxybenzoyl}-9H-carbazol-3-yl]-1-(O-acetyloxime), and the like.

A commercially available photo-radical generator may be used directly. Specific examples of a commercially available photo-radical generator include Irgacure 907, Irgacure 184, Irgacure 369, Irgacure 651, Irgacure 819, Irgacure OXE02 (manufactured by BASF), Adekaoptomer N1919 (manufactured by Adeka Corporation), and the like.

Examples of the anionic initiator include alkyllithium compounds; monolithium salts or monosodium salts of biphenyl, naphthalene, pyrene, and the like; polyfunctional initiators such as dilithiums and trilithium salts; and the like.

Examples of the cationic initiator include proton acids such as sulfuric acid, phosphoric acid, perchloric acid, and trifluoromethanesulfonic acid; Lewis acids such as boron trifluoride, aluminum chloride, titanium tetrachloride, and tin tetrachloride; an aromatic onium salt or a combination of an aromatic onium salt and a reducing agent; and the like.

These initiators may be used either alone or in combination.

The initiator is normally added to the polymerizable composition in an amount of 0.1 to 30 parts by weight, and preferably 0.5 to 10 parts by weight, based on 100 parts by weight of the polymerizable compound.

It is preferable to add a surfactant to the polymerizable composition according to one embodiment of the invention in order to adjust surface tension. The surfactant is not particularly limited, but is preferably a nonionic surfactant. A commercially available product may be used as the nonionic surfactant. Examples of the nonionic surfactant include a nonionic surfactant that is an oligomer having a molecular weight of about several thousand (e.g., "KH-40" manufactured by AGC Seimi Chemical Co., Ltd.), and the like. The surfactant is normally added to the polymerizable composition in an amount of 0.01 to 10 parts by weight, and preferably 0.1 to 2 parts by weight, based on 100 parts by weight of the polymerizable compound.

The polymerizable composition according to one embodiment of the invention may further include an additional additive such as an additional copolymerizable monomer, a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, or a metal oxide (e.g., titanium oxide). Each additive is normally added to the polymerizable composition in an amount of 0.1 to 20 parts by weight based on 100 parts by weight of the polymerizable compound.

The polymerizable composition according to one embodiment of the invention may be prepared by mixing and dissolving given amounts of the polymerizable compound according to one embodiment of the invention, the initiator, and an optional additive in an appropriate solvent.

Examples of the solvent include ketones such as cyclopentanone, cyclohexanone, and methyl ethyl ketone; esters such as butyl acetate and amyl acetate; halogenated hydrocarbons such as chloroform, dichloromethane, and dichloroethane; ethers such as 1,4-dioxane, cyclopentyl methyl ether, tetrahydrofuran, tetrahydropyran, and 1,3-dioxolane; and the like.

The polymerizable composition thus obtained is useful as a raw material for producing a polymer or an optically anisotropic article according to one embodiment of the invention (described below).

3) Polymer

A polymer according to one embodiment of the invention is (1) a polymer obtained by polymerizing the polymerizable compound according to one embodiment of the invention, or (2) a polymer obtained by polymerizing the polymerizable composition according to one embodiment of the invention.

The term "polymerization" used herein refers to a chemical reaction in a broad sense including a normal polymerization reaction and a crosslinking reaction.

(1) Polymer Obtained by Polymerizing Polymerizable Compound

The polymer obtained by polymerizing the polymerizable compound according to one embodiment of the invention may be a homopolymer of the polymerizable compound according to one embodiment of the invention, a copolymer of two or more types of the polymerizable compound according to one embodiment of the invention, or a copolymer of the polymerizable compound according to one embodiment of the invention and an additional copolymerizable monomer.

Examples of the additional copolymerizable monomer include, but are not limited to, 4'-methoxyphenyl 4-(2-methacryloyloxyethyloxy)benzoate, biphenyl 4-(6-methacryloyloxyhexyloxy)benzoate, 4'-cyanobiphenyl 4-(2-acryloyloxyethyloxy)benzoate, 4'-cyanobiphenyl 4-(2-methacryloyloxyethyloxy)benzoate, 3',4'-difluorophenyl 4-(2-methacryloyloxyethyloxy)benzoate, naphthyl 4-(2-methacryloyloxyethyloxy)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4"-fluorobenzyloxy)-biphenyl, 4-acryloyloxy-4'-propylcyclohexylphenyl, 4-methacryloyl-4'-butylbicyclohexyl, 4-acryloyl-4'-amytolan, 4-acryloyl-4'-(3,4-difluorophenyl)bicyclohexyl, (4-amylphenyl) 4-(2-acryloyloxyethyl)benzoate, (4-(4'-propylcyclohexyl)phenyl) 4-(2-acryloyloxyethyl)benzoate, and the like. Examples of a commercially available product of the additional copolymerizable monomer include LC-242 (manufactured by BASF).

A polyfunctional monomer that includes a plurality of polymerizable unsaturated groups (e.g., acryloyl group, methacryloyl group, vinyl group, and allyl group) may also be used as the additional copolymerizable monomer.

Examples of the polyfunctional monomer include alkanediol diacrylates such as 1,2-butanediol diacrylate, 1,3-butanediol diacrylate, 1,4-butanediol diacrylate, neopentanediol diacrylate, and 1,6-hexanediol diacrylate; alkanediol dimethacrylates such as 1,2-butanediol dimethacrylate, 1,3-butanediol dimethacrylate, 1,4-butanediol dimethacrylate, neopentanediol dimethacrylate, and 1,6-hexanediol dimethacrylate; polyethylene glycol diacrylates such as ethylene glycol diacrylate, diethylene glycol diacrylate, triethylene glycol diacrylate, and tetraethylene glycol diacrylate; polypropylene glycol diacrylates such as propylene glycol diacrylate, dipropylene glycol diacrylate, tripropylene glycol diacrylate, and tetrapropylene glycol diacrylate; polyethylene glycol dimethacrylates such as ethylene glycol dimethacrylate, diethylene glycol dimethacrylate, triethylene glycol dimethacrylate, and tetraethylene glycol dimethacrylate; polypropylene glycol dimethacrylates such as propylene glycol dimethacrylate, dipropylene glycol dimethacrylate, tripropylene glycol dimethacrylate, and tetrapropylene glycol dimethacrylate; polyethylene glycol divinyl ethers such as ethylene glycol divinyl ether, diethylene glycol divinyl ether, triethylene glycol divinyl ether, and tetraethylene glycol divinyl ether; polyethylene glycol diallyl ethers such as ethylene glycol diallyl ether, diethylene glycol diallyl ether, triethylene glycol diallyl ether, and tetraethylene glycol diallyl ether; bisphenol F ethoxylate diacrylate, bisphenol F ethoxylate dimethacrylate, bisphenol A ethoxylate diacrylate, bisphenol A ethoxylate dimethacrylate, trimethylolpropane triacrylate, trimethylolpropane trimethacrylate, trimethylolpropane ethoxylate triacylate, trimethylolpropane ethoxylate trimethacrylate, trimethylolpropane propoxylate triacylate, trimethylolpropane propoxylate trimethacrylateisocyanuric acid ethoxylate triacylate, glycerol ethoxylate triacylate, glycerol propoxy late triacylate, pentaerythritol ethoxylate tetraacrylate, ditrimethylolpropane ethoxylate tetraacrylate, dipentaerythritol ethoxylate hexacrylate, and the like.

The polymerizable compound according to one embodiment of the invention may be (co)polymerized together with an optional additional copolymerizable monomer in the presence of an appropriate initiator. The initiator is used in an amount similar to that of the initiator included in the polymerizable composition.

When the polymer according to one embodiment of the invention is a copolymer of the polymerizable compound according to one embodiment of the invention and the additional copolymerizable monomer, the content of constituent units derived from the polymerizable compound according to one embodiment of the invention is not particularly limited, but is preferably 50 wt % or more, and more preferably 70 wt % or more, based on the amount of the total constituent units. If the content of constituent units derived from the polymerizable compound is within the above range, a polymer that has a high glass transition temperature (Tg) and high hardness can be obtained.

The polymer (1) may be produced by (A) (co)polymerizing the polymerizable compound together with an optional additional copolymerizable monomer in an appropriate organic solvent in the presence of an appropriate initiator, isolating the target polymer, dissolving the polymer in an appropriate organic solvent to prepare a solution, applying the solution to an appropriate substrate to obtain a film, and drying the film, followed by optional heating, or (B) applying a solution prepared by dissolving the polymerizable compound in an organic solvent together with an optional additional copolymerizable monomer to a substrate by a known coating method, removing the solvent, and effecting polymerization by applying heat or activated energy rays, for example.

Examples of the initiator include those mentioned above in connection with the initiator included in the polymerizable composition.

The organic solvent used for the method (A) is not particularly limited as long as the organic solvent is inert. Examples of the organic solvent used for the method (A) include aromatic hydrocarbons such as toluene, xylene, and mesitylene; ketones such as cyclohexanone, cyclopentanone, and methyl ethyl ketone; acetates such as butyl acetate and amyl acetate; halogenated hydrocarbons such as chloroform, dichloromethane, and dichloroethane; ethers such as cyclopentyl methyl ether, tetrahydrofuran, and tetrahydropyran; and the like. Among these, it is preferable to use a compound having a boiling point of 60 to 250° C., and preferably 60 to 150° C., from the viewpoint of handling capability.

Examples of the organic solvent used to dissolve the polymer include ketones such as acetone, methyl ethyl ketone, methyl isobutyl ketone, cyclopentanone, and cyclohexanone; esters such as butyl acetate and amyl acetate; halogenated hydrocarbons such as dichloromethane, chloroform, and dichloroethane; ethers such as tetrahydrofuran, tetrahydropyran, 1,2-dimethoxyethane, 1,4-dioxane, and cyclopentyl methyl ether; and the like.

Examples of the organic solvent used for the method (B) include ketones such as acetone, methyl ethyl ketone, methyl isobutyl ketone, cyclopentanone, and cyclohexanone; esters such as butyl acetate and amyl acetate; halogenated hydrocarbons such as dichloromethane, chloroform, and dichloroethane; ethers such as tetrahydrofuran (THF), tetrahydropyran, 1,2-dimethoxyethane, 1,4-dioxane, cyclopentyl methyl ether, 1,3-dioxolane; and the like. Among these, it is preferable to use a compound having a boiling point of 60 to 200° C. from the viewpoint of handling capability.

A substrate formed of a known organic or inorganic material may be used as the substrate. Examples of the organic material include polycycloolefins (e.g., Zeonex, Zeonor (registered trademark; manufactured by Zeon Corporation), Arton (registered trademark; manufactured by JSR Corporation), and Apel (registered trademark; manufactured by Mitsui Chemicals Inc.)), polyethylene terephthalate, polycarbonate, polyimide, polyamide, polymethyl methacrylate, polystyrene, polyvinyl chloride, polytetrafluoroethylene, cellulose, cellulose triacetate, polyethersulfone, and the like. Examples of the inorganic material include silicon, glass, calcite, and the like. It is preferable to use an organic material.

The substrate may be a single-layer substrate, or may be a laminate.

The substrate is preferably a substrate formed of an organic material, and more preferably a resin film formed of an organic material.

The polymer solution (method (A)) or the solution subjected to polymerization may be applied to the substrate by a known coating method. Examples of the coating method include a curtain coating method, an extrusion coating method, a roll coating method, a spin coating method, a dip coating method, a bar coating method, a spray coating method, a slide coating method, a print coating method, and the like.

(2) Polymer Obtained by Polymerizing Polymerizable Composition

The polymer according to one embodiment of the invention can be easily obtained by polymerizing the polymerizable composition according to one embodiment of the invention. It is preferable to use a polymerizable composition that includes the above initiator (particularly a photoinitiator) from the viewpoint of ensuring an efficient polymerization reaction.

It is preferable to produce the polymer according to one embodiment of the invention by applying the polymerizable composition according to one embodiment of the invention to a substrate, and polymerizing the applied polymerizable composition (i.e., method (B)). Examples of the substrate include a substrate used to produce an optically anisotropic article (described later).

The polymerizable composition according to one embodiment of the invention may be applied to the substrate by a known coating method (e.g., bar coating method, spin coating method, roll coating method, gravure coating method, spray coating method, die coating method, cap coating method, or dipping method). A known organic solvent may be added to the polymerizable composition in order to improve the applicability of the polymerizable composition. In this case, it is preferable to remove the organic solvent by air-drying, drying by heating, drying under reduced pressure, drying by heating under reduced pressure, or the like after applying the polymerizable composition to the substrate.

The polymerizable compound or the polymerizable composition according to one embodiment of the invention may be polymerized by applying activated energy rays, applying heat, or the like. It is preferable to polymerize the polymerizable compound or the polymerizable composition by applying activated energy rays since heating is unnecessary, and the reaction proceeds at room temperature. It is preferable to apply light (e.g., ultraviolet rays) from the viewpoint of convenience.

The temperature during application of activated energy rays is preferably 30° C. or less. The UV dose is normally 1 $W/m^2$ to 10 $kW/m^2$, and preferably 5 $W/m^2$ to 2 $kW/m^2$.

A polymer obtained by polymerizing the polymerizable compound or the polymerizable composition according to one embodiment of the invention may be used after removing the polymer from the substrate, or may be used directly as an optical film organic material or the like without removing the polymer from the substrate.

The number average molecular weight of the polymer according to one embodiment of the invention thus obtained is preferably 500 to 500,000, and more preferably 5000 to 300,000. When the number average molecular weight of the polymer is within the above range, the resulting film exhibits high hardness and an excellent handling capability. The number average molecular weight of the polymer may be determined by gel permeation chromatography (GPC) using monodisperse polystyrene as a standard (eluant: THF).

It is considered that the polymer according to one embodiment of the invention has uniform crosslinking points in the molecule, and exhibits high crosslinking efficiency and excellent hardness.

The polymer according to one embodiment of the invention makes it possible to inexpensively obtain an optical film that achieves uniform conversion of polarized light over a wide wavelength band.

4) Optically Anisotropic Article

An optically anisotropic article according to one embodiment of the invention includes the polymer according to one embodiment of the invention.

The optically anisotropic article according to one embodiment of the invention may be obtained by forming an alignment film on a substrate, and forming a liquid crystal layer on the alignment film using the polymer according to one embodiment of the invention.

The alignment film is formed on the surface of the substrate in order to achieve in-plane alignment of an organic semiconductor compound in one direction.

The alignment film includes a polymer such as a polyimide, polyvinyl alcohol, polyester, polyallylate, polyamideimide, or polyetherimide. The alignment film may be obtained by applying a solution (alignment film composition) that includes such a polymer to the substrate to form a film, drying the film, and performing a rubbing treatment in one direction, for example.

The thickness of the alignment film is preferably 0.001 to 5 μm, and more preferably 0.001 to 1 μm.

The rubbing treatment may be performed on the alignment film or the substrate. The rubbing treatment may be implemented by an arbitrary method. For example, the alignment film may be rubbed in a given direction using a roll around which a cloth or felt formed of synthetic fibers (e.g., nylon) or natural fibers (e.g., cotton) is wound. It is preferable to wash the alignment film with isopropyl alcohol or the like after the rubbing treatment in order to remove fine powder (foreign substance) formed during the rubbing treatment to clean the surface of the alignment film.

The alignment film may be provided with a function of achieving in-plane alignment of a cholesteric liquid crystal layer by applying polarized UV rays to the surface of the alignment film.

The liquid crystal layer may be formed on the alignment film using the polymer according to one embodiment of the invention using the method described above in connection with the polymer according to one embodiment of the invention.

Since the optically anisotropic article according to one embodiment of the invention is produced using the polymer according to one embodiment of the invention, the optically anisotropic article can be produced at low cost, achieves uniform conversion of polarized light over a wide wavelength band, and shows satisfactory performance.

Examples of the optically anisotropic article according to one embodiment of the invention include a retardation film, an alignment film for liquid crystal display elements, a polarizer, a viewing angle enhancement film, a color filter, a low-pass filter, an optical polarization prism, an optical filter, and the like.

EXAMPLES

The invention is further described below by way of examples. Note that the invention is not limited to the following examples.

Example 1

Synthesis of Compound 1

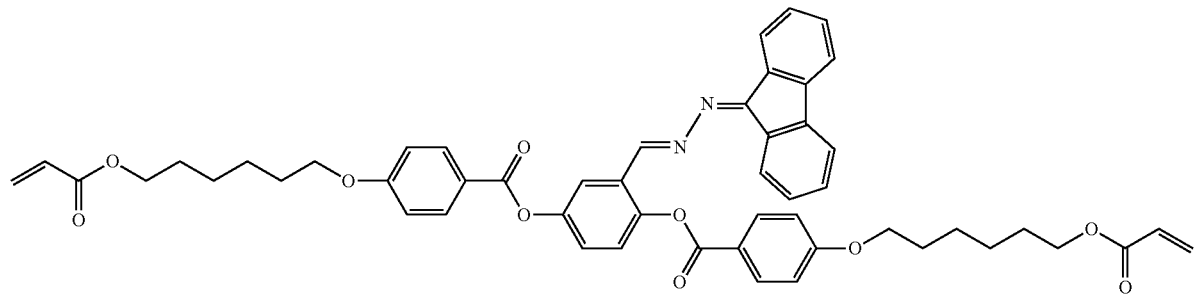

Compound 1

Step 1: Synthesis of Intermediate A

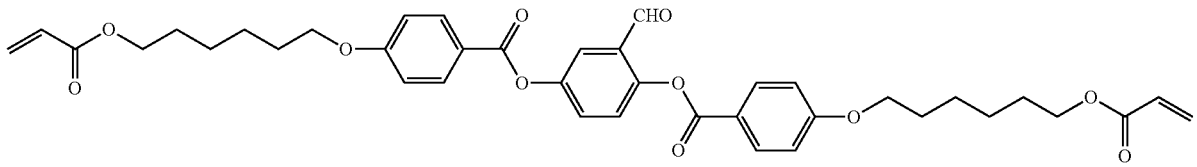 [SMILES: C=CC(=O)OCCCCCCOc1ccc(C(=O)Oc2ccc(OC(=O)c3ccc(OCCCCCCOC(=O)C=C)cc3)c(C=O)c2)cc1]

Intermediate A

A four-necked reactor equipped with a thermometer was charged with 20 g (144.8 mmol) of 2,5-dihydroxybenzaldehyde, 105.8 g (362.0 mmol) of 4-(6-acryloyl-hex-1-yloxy) benzoic acid (manufactured by DKSH Japan K.K.), 5.3 g (43.4 mmol) of 4-(dimethylamino)pyridine, and 200 ml of N-methylpyrrolidone under a nitrogen stream. After the addition of 83.3 g (434.4 mmol) of 1-ethyl-3-(3-dimethylaminopropyl)carbodiimide hydrochloride (WSC), the mixture was stirred at 25° C. for 12 hours. After completion of the reaction, the reaction mixture was added to 1.5 l of water, and extracted with 500 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=9:1 (volume ratio)) to obtain 75 g of an intermediate A as a white solid (yield: 75.4%).

The structure of the intermediate A was identified by $^1$H-NMR.

$^1$H-NMR (400 MHz, CDCl$_3$, TMS, δ ppm): 10.20 (s, 1H), 8.18-8.12 (m, 4H), 7.78 (d, 1H, J=2.8 Hz), 7.52 (dd, 1H, J=2.8 Hz, 8.7 Hz), 7.38 (d, 1H, J=8.7 Hz), 7.00-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 4.18 (t, 4H, J=6.4 Hz), 4.08-4.04 (m, 4H), 1.88-1.81 (m, 4H), 1.76-1.69 (m, 4H), 1.58-1.42 (m, 8H).

Step 2: Synthesis of Intermediate B

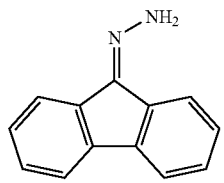 [SMILES: NN=C1c2ccccc2-c2ccccc21]

Intermediate B

A four-necked reactor equipped with a thermometer was charged with 5 g (27.7 mmol) of 9-fluorenone, 13.9 g (277.7 mmol) of hydrazine monohydrate, and 50 ml of 1-propanol under a nitrogen stream, and the mixture was stirred at 25° C. for 16 hours. After completion of the reaction, a solid that precipitated was filtered off, washed with 1-propanol, and air-dried to obtain 2.2 g of an intermediate B as a yellow solid. The intermediate B was used directly for the subsequent reaction without purification.

Step 3: Synthesis of Compound 1

A four-necked reactor equipped with a thermometer was charged with 3.0 g (4.37 mmol) of the intermediate A synthesized in the step 1, 1.1 g (5.68 mmol) of the intermediate B synthesized in the step 2, 80 ml of ethanol, and 40 ml of THF under a nitrogen stream. A solution prepared by dissolving 0.1 g (0.44 mmol) of (±)-10-camphorsulfonic acid in 3 ml of THF was slowly added to the solution, and the mixture was stirred at 25° C. for 2 hours. After completion of the reaction, the reaction mixture was added to 300 ml of saturated sodium bicarbonate water, and extracted twice with 100 ml of chloroform. The chloroform layer was washed with 200 ml of a saturated sodium chloride solution, and dried over anhydrous sodium sulfate, and sodium sulfate was filtered off. Chloroform was evaporated from the filtrate under reduced pressure using a rotary evaporator to obtain a yellow solid. The yellow solid was purified by silica gel column chromatography (toluene:ethyl acetate=8:2 (volume ratio)) to obtain 1.8 g of a compound 1 as a yellow solid (yield: 47.7%).

The structure of the target product was identified by $^1$H-NMR.

$^1$H-NMR (400 MHz, CDCl$_3$, TMS, δ ppm): 8.65 (s, 1H), 8.29 (d, 1H, J=7.3 Hz), 8.21-8.16 (m, 5H), 7.82 (d, 1H, J=7.3 Hz), 7.60-7.57 (m, 2H), 7.43-7.25 (m, 6H), 7.01-6.96 (m, 4H), 6.402 (dd, 1H, J=1.8 Hz, 17.4 Hz), 6.398 (dd, 1H, J=1.8 Hz, 17.4 Hz), 6.122 (dd, 1H, J=10.5 Hz, 17.4 Hz), 6.117 (dd, 1H, J=10.5 Hz, 17.4 Hz), 5.820 (dd, 1H, J=1.8 Hz, 10.5 Hz), 5.816 (dd, 1H, J=1.8 Hz, 10.5 Hz), 4.18 (t, 2H, J=6.6 Hz), 4.17 (t, 2H, J=6.6 Hz), 4.06 (t, 2H, J=6.4 Hz), 4.05 (t, 2H, J=6.4 Hz), 1.87-1.80 (m, 4H), 1.76-1.68 (m, 4H), 1.59-1.42 (m, 8H).

Example 2

Synthesis of Compound 2

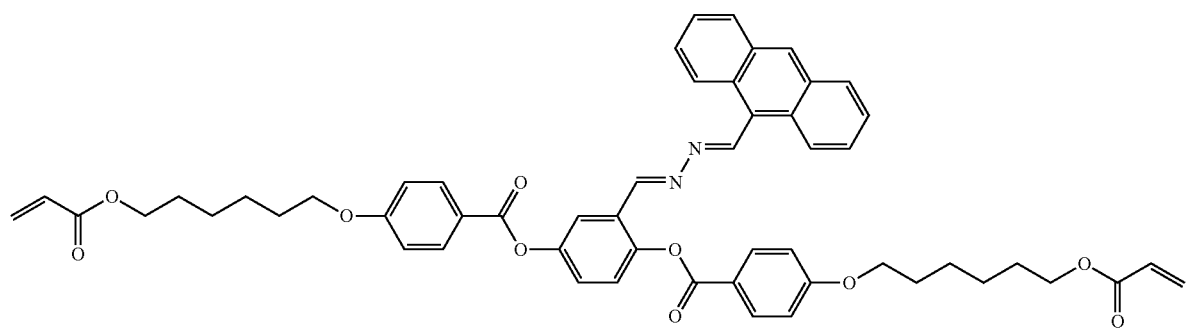

Compound 2

Step 1: Synthesis of Intermediate C

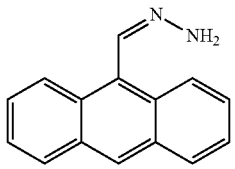 [SMILES: N/N=C\c1c2ccccc2cc2ccccc12]

Intermediate C

A four-necked reactor equipped with a thermometer was charged with 3.6 g (71.9 mol) of hydrazine monohydrate and 30 ml of ethanol under a nitrogen stream. A solution prepared by dissolving 3 g (14.5 mmol) of 9-anthracene carbaldehyde in 30 ml of THF was slowly added to the solution. The mixture was then stirred at 25° C. for 1.5 hours. After completion of the reaction, the reaction mixture was added to 200 ml of saturated sodium bicarbonate water, and extracted twice with 100 ml of chloroform. The chloroform layer was washed with 200 ml of a saturated sodium chloride solution, and dried over anhydrous sodium sulfate, and sodium sulfate was filtered off. Chloroform was evaporated from the filtrate under reduced pressure using a rotary evaporator, and the resulting solid was dried to obtain 2.5 g of an intermediate C as a yellow solid. The intermediate C was used directly for the subsequent reaction without purification.

Step 2: Synthesis of Compound 2

A four-necked reactor equipped with a thermometer was charged with 3.0 g (4.37 mmol) of the intermediate A synthesized in the step 1 (see Synthesis of compound 1), 1.2 g (5.24 mmol) of the intermediate C synthesized in the step 1, and 30 ml of THF under a nitrogen stream. A solution prepared by dissolving 0.1 g (0.44 mmol) of (±)-10-camphorsulfonic acid in 3 ml of THF was slowly added to the solution, and the mixture was stirred at 25° C. for 2 hours. After completion of the reaction, the reaction mixture was added to 300 ml of saturated sodium bicarbonate water, and extracted twice with 100 ml of ethyl acetate. The ethyl acetate layer was washed with 200 ml of a saturated sodium chloride solution, and dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 2.1 g of a compound 2 as a yellow solid (yield: 54.1%).

The structure of the target product was identified by $^1$H-NMR.

$^1$H-NMR (400 MHz, CDCl$_3$, TMS, δ ppm): 9.74 (s, 1H), 8.95 (s, 1H), 8.57-8.53 (m, 3H), 8.20-8.18 (m, 4H), 8.14 (d, 1H, J=2.7 Hz), 8.02-8.00 (m, 2H), 7.56-7.47 (m, 4H), 7.42 (dd, 1H, J=2.7 Hz, 8.7 Hz), 7.36 (d, 1H, J=8.7 Hz), 7.00-6.96 (m, 4H), 6.404 (dd, 1H, J=1.4 Hz, 17.4 Hz), 6.384 (dd, 1H, J=1.4 Hz, 17.4 Hz), 6.126 (dd, 1H, J=8.7 Hz, 17.4 Hz), 6.100 (dd, 1H, J=8.7 Hz, 17.4 Hz), 5.824 (dd, 1H, J=1.4 Hz, 8.7 Hz), 5.798 (dd, 1H, J=1.4 Hz, 8.7 Hz), 4.18 (t, 2H, J=6.4 Hz), 4.16 (t, 2H, J=6.4 Hz), 4.07 (t, 2H, J=6.4 Hz), 4.02 (t, 2H, J=6.4 Hz), 1.89-1.78 (m, 4H), 1.77-1.66 (m, 4H), 1.58-1.44 (m, 8H)

Example 3

Synthesis of Compound 3

Step 1: Synthesis of Intermediate D

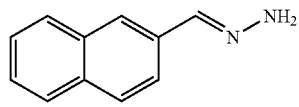 [SMILES: N/N=C/c1ccc2ccccc2c1]

Intermediate D

A four-necked reactor equipped with a thermometer was charged with 4.8 g (95.9 mol) of hydrazine monohydrate and 25 ml of ethanol under a nitrogen stream. A solution prepared by dissolving 3 g (19.2 mmol) of 2-naphthaldehyde in 25 ml of THF was slowly added to the solution, and the mixture was stirred at 25° C. for 2 hours. After completion of the reaction, the reaction mixture was added to 200 ml of saturated sodium bicarbonate water to precipitate a solid. The solid was then filtered off by suction filtration. The solid was then washed with water, and air-dried to obtain 2.5 of an intermediate D as a yellow solid (yield: 76.5%). The intermediate D was used directly for the subsequent reaction without purification.

Step 2: Synthesis of Compound 3

A four-necked reactor equipped with a thermometer was charged with 3.0 g (4.37 mmol) of the intermediate A synthesized in the step 1 (see Synthesis of compound 1), 0.89 g (5.24 mmol) of the intermediate D synthesized in the step 1, 30 ml of THF, and 10 ml of ethanol under a nitrogen stream. A solution prepared by dissolving 0.1 g (0.44 mmol) of (±)-10-camphorsulfonic acid in 3 ml of THF was slowly added to the solution, and the mixture was stirred at 25° C. for 2 hours. After completion of the reaction, the reaction mixture was added to 200 ml of saturated sodium bicarbonate water, and extracted twice with 100 ml of ethyl acetate. The ethyl acetate layer was washed with 200 ml of a saturated sodium chloride solution, and dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 1.6 g of a compound 3 as a light yellow solid (yield: 43.6%).

The structure of the target product was identified by $^1$H-NMR.

Compound 3

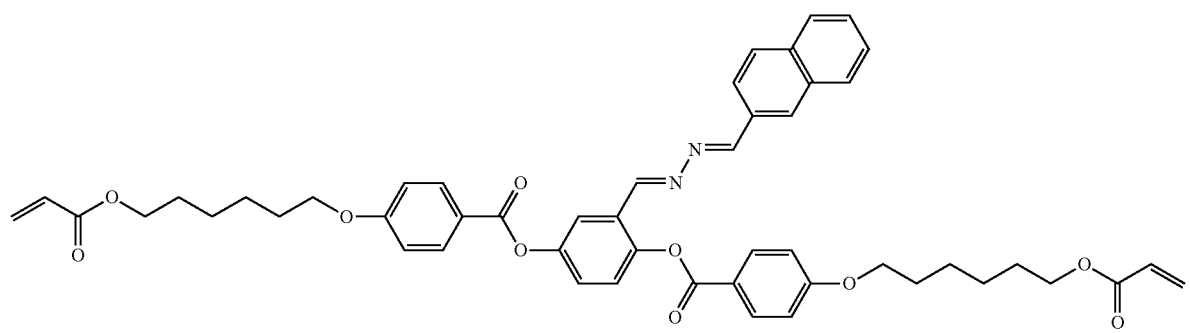

¹H-NMR (400 M Hz, CDCl₃, TMS, δ ppm): 8.82 (s, 1H), 8.70 (s, 1H), 8.22-8.15 (m, 4H), 8.085-8.078 (m, 2H), 8.02 (dd, 1H, J=1.8 Hz, 8.7 Hz), 7.89-7.83 (m, 3H), 7.55-7.49 (m, 2H), 7.39 (dd, 1H, J=2.8 Hz, 8.7 Hz), 7.32 (d, 1H, J=8.7 Hz), 7.02-6.97 (m, 4H), 6.40 (dd, 2H, J=1.8 Hz, 17.3 Hz), 6.13 (dd, 2H, J=10.6 Hz, 17.3 Hz), 5.824 (dd, 1H, J=1.8 Hz, 10.6 Hz), 5.819 (dd, 1H, J=1.8 Hz, 10.6 Hz), 4.19 (t, 4H, J=6.4 Hz), 4.08 (t, 2H, J=6.4 Hz), 4.06 (t, 2H, J=6.4 Hz), 1.89-1.82 (m, 4H), 1.77-1.70 (m, 4H), 1.59-1.44 (m, 8H).

Example 4

Synthesis of Compound 4

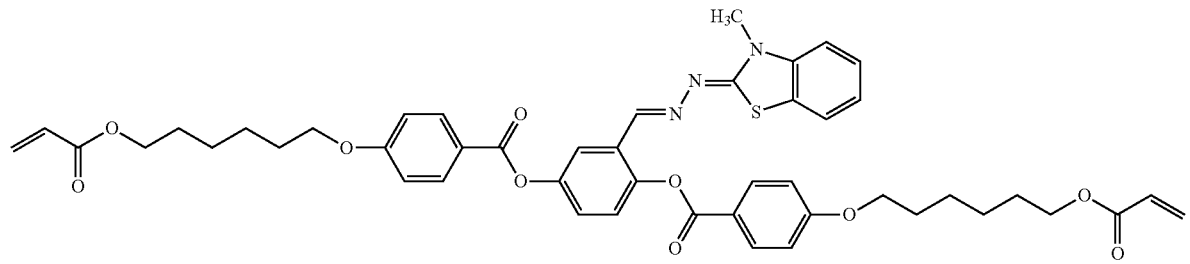

Compound 4

Step 1: Synthesis of Intermediate E

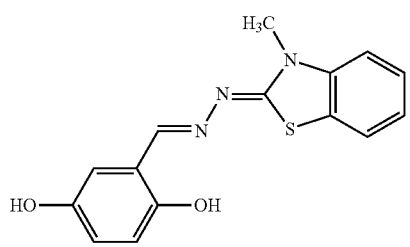 [SMILES: Cn1/c(=N/N=C/c2cc(O)ccc2O)sc2ccccc21]

Intermediate E

A four-necked reactor equipped with a thermometer was charged with 6 g (27.8 mmol) of 3-methyl-2-benzothiazolinonehydrazone hydrochloride hydrate (manufactured by Tokyo Chemical Industry Co., Ltd.), 1.9 g (13.9 mmol) of 2,5-dihydroxybenzaldehyde, and 100 ml of 1-propanol under a nitrogen stream, and the mixture was refluxed for 1 hour with heating. After completion of the reaction, the reaction mixture was cooled to room temperature. THF was then added to the reaction mixture to obtain a homogeneous solution. The solution was added dropwise to 10% sodium bicarbonate water to precipitate a solid. The solid was filtered off by suction filtration. The solid was then washed with water, and dried using a vacuum dryer to obtain 2.8 of an intermediate E as a yellow solid (yield: 67.3%).

The structure of the target product was identified by ¹H-NMR.

¹H-NMR (400 MHz, DMSO-d₆, TMS, δ ppm): 10.21 (s, 1H), 8.95 (s, 1H), 8.50 (s, 1H), 7.65 (d, 1H, J=7.8 Hz), 7.35-7.28 (m, 2H), 7.11-7.07 (m, 1H), 6.92 (d, 1H, J=2.3 Hz), 6.74-6.68 (m, 2H), 3.54 (s, 3H)

Step 2: Synthesis of Compound 4

A four-necked reactor equipped with a thermometer was charged with 1.8 g (6.0 mmol) of the intermediate E synthesized in the step 1, 5.3 g (18.0 mmol) of 4-(6-acryloyl-hex-1-yloxy)benzoic acid (manufactured by DKSH Japan K.K.), 0.26 g (2.2 mmol) of 4-(dimethylamino)pyridine, and 80 ml of N-methylpyrrolidone under a nitrogen stream. After the addition of 4.1 g (21.6 mmol) of 1-ethyl-3-(3-dimethylaminopropyl)carbodiimide hydrochloride (WSC), the mixture was stirred at 25° C. for 15 hours. After completion of the reaction, the reaction mixture was added to 500 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 3.3 g of a compound 4 as a yellow solid (yield: 64.9%).

The structure of the target product was identified by ¹H-NMR.

¹H-NMR (400 MHz, CDCl₃, TMS, δ ppm): 8.48 (s, 1H), 8.18 (d, 4H, J=8.7 Hz), 7.99 (d, 1H, J=1.8 Hz), 7.36 (d, 1H, J=7.8 Hz), 7.27-7.22 (m, 3H), 7.06-7.02 (m, 1H), 7.00-6.96 (m, 5H), 6.40 (dd, 2H, J=1.4 Hz, 17.4 Hz), 6.13 (dd, 2H, J=10.5 Hz, 17.4 Hz), 5.82 (dd, 2H, J=1.4 Hz, 10.5 Hz), 4.18 (t, 4H, J=6.2 Hz), 4.06 (t, 4H, J=6.2 Hz), 3.55 (s, 3H), 1.89-1.82 (m, 4H), 1.77-1.70 (m, 4H), 1.58-1.43 (m, 8H).

Example 5

Synthesis of Compound 5

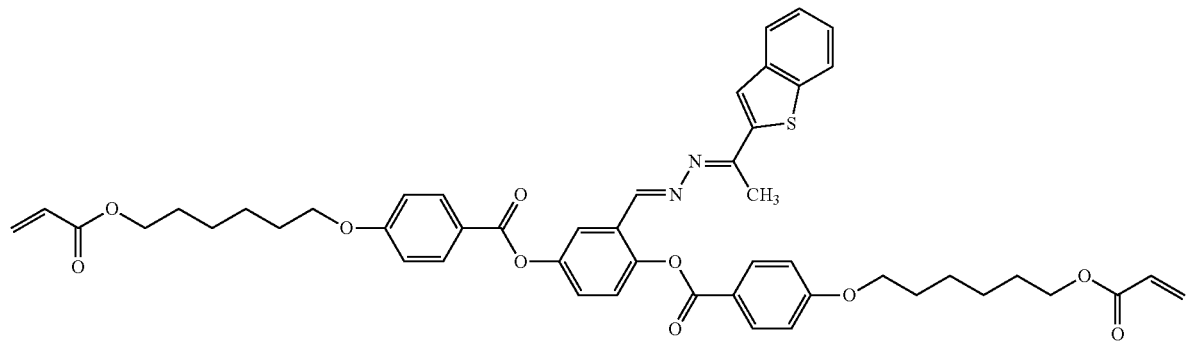

Compound 5

Step 1: Synthesis of Intermediate F

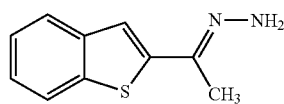

Intermediate F

A four-necked reactor equipped with a thermometer was charged with 11.4 g (227.7 mol) of hydrazine monohydrate, 4.0 g (22.7 mmol) of 2-acetylbenzo[b]thiophene, and 50 ml of ethanol under a nitrogen stream, and the mixture was refluxed for 1.5 hours with heating. The reaction mixture was then cooled to room temperature, and added to 10% sodium bicarbonate water to precipitate crystals. The crystals were filtered off by suction filtration. The crystals were then washed with water, air-dried, and used directly for the subsequent reaction without purification.

Step 2: Synthesis of Compound 5

A four-necked reactor equipped with a thermometer was charged with 3.0 g (4.37 mmol) of the intermediate A synthesized in the step 1 (see Synthesis of compound 1), 1.0 g (5.24 mmol) of the intermediate F synthesized in the step 1, 30 ml of THF, and 15 ml of ethanol under a nitrogen stream. A solution prepared by dissolving 0.1 g (0.44 mmol) of (±)-10-camphorsulfonic acid in 3 ml of THF was slowly added to the solution, and the mixture was stirred at 25° C. for 2 hours. After completion of the reaction, the reaction mixture was added to 200 ml of saturated sodium bicarbonate water, and extracted twice with 100 ml of ethyl acetate. The ethyl acetate layer was washed with 200 ml of a saturated sodium chloride solution, and dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 2.2 g of a compound 5 as a yellow solid (yield: 58.6%).

The structure of the target product was identified by $^1$H-NMR.

$^1$H-NMR (400 MHz, CDCl$_3$, TMS, δ ppm): 8.61 (s, 1H), 8.19-8.15 (m, 4H), 8.04 (d, 1H, J=2.7 Hz), 7.67 (s, 1H), 7.79-7.75 (m, 2H), 7.37-7.29 (m, 4H), 7.01-6.96 (m, 4H), 6.405 (dd, 1H, J=1.4 Hz, 17.4 Hz), 6.402 (dd, 1H, J=1.4 Hz, 17.4 Hz), 6.14 (dd, 1H, J=10.5 Hz, 17.4 Hz), 6.11 (dd, 1H, J=10.5 Hz, 17.4 Hz), 5.822 (dd, 1H, J=1.4 Hz, 10.5 Hz), 5.818 (dd, 1H, J=10.5 Hz), 4.18 (t, 4H, J=6.4 Hz), 4.062 (t, 2H, J=6.4 Hz), 4.058 (t, 2H, J=6.4 Hz), 2.52 (s, 3H), 1.88-1.81 (m, 4H), 1.76-1.69 (m, 4H), 1.58-1.43 (m, 8H).

Example 6

Synthesis of Compound 6

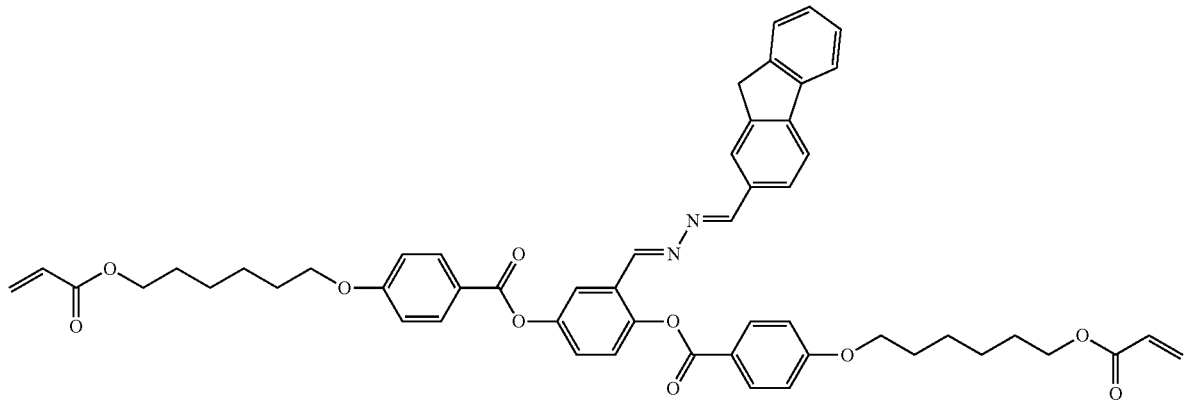

Compound 6

Step 1: Synthesis of Intermediate G

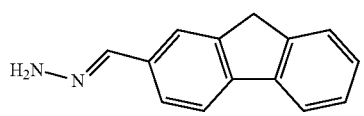 [SMILES: N/N=C/c1ccc2c(c1)Cc1ccccc1-2]

Intermediate G

A four-necked reactor equipped with a thermometer was charged with 1.9 g (38.6 mmol) of hydrazine monohydrate and 15 ml of ethanol under a nitrogen stream. After the addition of 1.5 g (7.72 mmol) of 2-fluorenecarbaldehyde, the mixture was stirred at 25° C. for 6 hours. After completion of the reaction, the reaction mixture was added to 50 ml of saturated sodium bicarbonate water, and extracted twice with 50 ml of chloroform. The chloroform layer was washed with 50 ml of a saturated sodium chloride solution, and dried over anhydrous sodium sulfate, and sodium sulfate was filtered off Chloroform was evaporated from the filtrate under reduced pressure using a rotary evaporator to obtain 1.2 g of an intermediate G as a yellow solid. The solid was then dried, and used directly for the subsequent reaction without purification.

Step 2: Synthesis of Compound 6

A four-necked reactor equipped with a thermometer was charged with 1.5 g (2.18 mmol) of the intermediate A synthesized in the step 1 (see Synthesis of compound 1), 683 mg (3.68 mmol) of the intermediate G synthesized in the step 1, 15 ml of THF, and 5 ml of ethanol under a nitrogen stream, and the mixture was stirred at 25° C. for 3 hours. After completion of the reaction, the reaction mixture was added to 100 ml of saturated sodium bicarbonate water, and extracted twice with 100 ml of chloroform. The chloroform layer was washed with 100 ml of a saturated sodium chloride solution, and dried over anhydrous sodium sulfate, and sodium sulfate was filtered off. Chloroform was evaporated from the filtrate under reduced pressure using a rotary evaporator to obtain a light yellow solid. The light yellow solid was purified by silica gel column chromatography (toluene:ethyl acetate=95:5 (volume ratio)) to obtain 117 mg of a compound 6 as a light yellow solid (yield: 14.2%).

The structure of the target product was identified by $^1$H-NMR.

$^1$H-NMR (400 MHz, CDCl$_3$, TMS, δ ppm): 8.80 (s, 1H), 8.63 (s, 1H), 8.20 (d, 2H, J=8.7 Hz), 8.16 (d, 2H, J=8.7 Hz), 8.07 (d, 1H, J=2.8 Hz), 8.00 (s, 1H), 7.80-7.85 (m, 2H), 7.74 (d, 1H, J=8.2 Hz), 7.55 (d, 1H, J=7.3 Hz), 7.30-7.40 (m, 4H), 7.00 (d, 2H, J=9.2 Hz), 6.98 (d, 2H, J=9.2 Hz), 6.41 (dd, 2H, J=1.4 Hz, 17.4 Hz), 6.13 (dd, 2H, J=10.5 Hz, 17.4 Hz), 5.82 (dd, 2H, J=1.4 Hz, 10.5 Hz), 4.190 (t, 2H, J=6.4 Hz), 4.186 (t, 2H, J=6.4 Hz), 4.08 (t, 2H, J=6.4 Hz), 4.06 (t, 2H, J=6.4 Hz), 3.92 (s, 2H), 1.80-1.90 (m, 4H), 1.70-1.77 (m, 4H), 1.43-1.60 (m, 8H).

Example 7

Synthesis of Compound 7

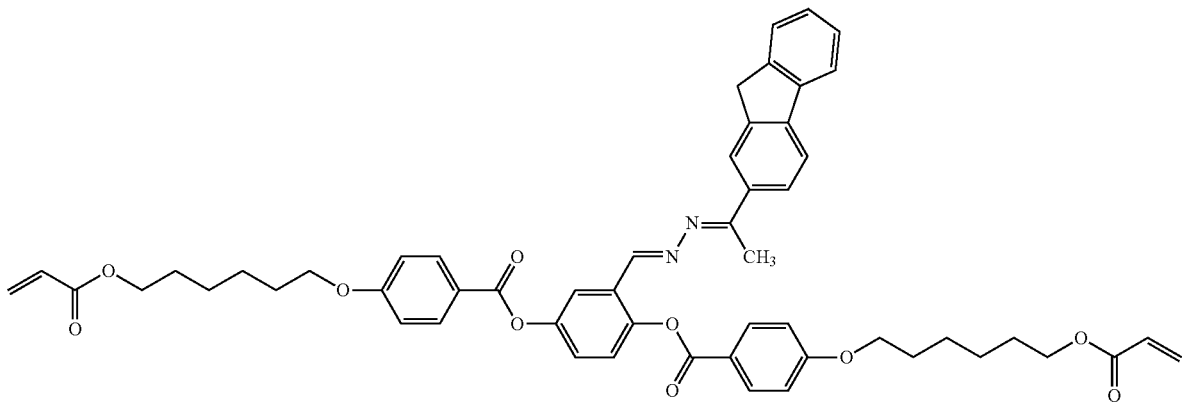

Compound 7

Step 1: Synthesis of Intermediate H

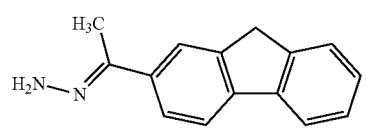 [SMILES: C/C(=N\N)c1ccc2c(c1)Cc1ccccc1-2]

Intermediate H

A four-necked reactor equipped with a thermometer was charged with 7.0 ml (114 mmol) of hydrazine monohydrate and 20 ml of propanol under a nitrogen stream. After the addition of 3.0 g (14.4 mmol) of 2-acetylfluorene, the mixture was refluxed for 6 hours with heating. The reaction mixture was then cooled to room temperature, added to 100 ml of saturated sodium bicarbonate water, and extracted twice with 100 ml of chloroform. The chloroform layer was washed with 100 ml of a saturated sodium chloride solution, and dried over anhydrous sodium sulfate, and sodium sulfate was filtered off. Chloroform was evaporated from the filtrate under reduced pressure using a rotary evaporator to obtain 2.8 g of an intermediate H as a yellow solid. The solid was then dried, and used directly for the subsequent reaction without purification.

Step 2: Synthesis of Compound 7

A four-necked reactor equipped with a thermometer was charged with 1.5 g (2.18 mmol) of the intermediate A synthesized in the step 1 (see Synthesis of compound 1), 632 mg (2.83 mmol) of the intermediate H synthesized in the step 1, 10 ml of THF, and 10 ml of ethanol under a nitrogen stream, and the mixture was refluxed for 8 hours with heating. The reaction mixture was then cooled to room temperature, added to 100 ml of saturated sodium bicarbonate water, and extracted twice with 50 ml of chloroform. The chloroform layer was washed with 50 ml of a saturated sodium chloride solution, and dried over anhydrous sodium sulfate, and sodium sulfate was filtered off. Chloroform was evaporated from the filtrate under reduced pressure using a rotary evaporator to obtain a light yellow solid. The light yellow solid was purified by silica gel column chromatography (toluene:ethyl acetate=90:10 (volume ratio)) to obtain 370 mg of a compound 7 as a light yellow solid (yield: 19.0%).

The structure of the target product was identified by $^1$H-NMR.

$^1$H-NMR (400 MHz, CDCl$_3$, TMS, δ ppm): 8.58 (s, 1H), 8.17 (d, 4H, J=8.7 Hz), 8.04-8.07 (m, 2H), 7.86 (d, 1H, J=8.7 Hz), 7.79 (dd, 2H, J=8.2 Hz, 8.7 Hz), 7.54 (d, 1H, J=7.8 Hz), 7.28-7.41 (m, 4H), 6.983 (d, 2H, J=8.7 Hz), 6.975 (d, 2H, J=8.7 Hz), 6.40 (dd, 1H, J=1.4 Hz, 17.4 Hz), 6.39 (dd, 1H, J=1.4 Hz, 17.4 Hz), 6.12 (dd, 1H, J=10.5 Hz, 17.4 Hz), 6.11 (dd, 1H, J=10.5 Hz, 17.4 Hz), 5.82 (dd, 1H, J=1.4 Hz, 10.5 Hz), 5.81 (dd, 1H, J=1.4 Hz, 10.5 Hz), 4.18 (t, 2H, J=6.4 Hz), 4.17 (t, 2H, J=6.4 Hz), 4.06 (t, 2H, J=6.2 Hz), 4.05 (t, 2H, J=6.4 Hz), 3.91 (s, 2H), 2.50 (s, 3H), 1.81-1.88 (m, 4H), 1.68-1.76 (m, 4H), 1.43-1.55 (m, 8H).

Example 8

Synthesis of Compound 8

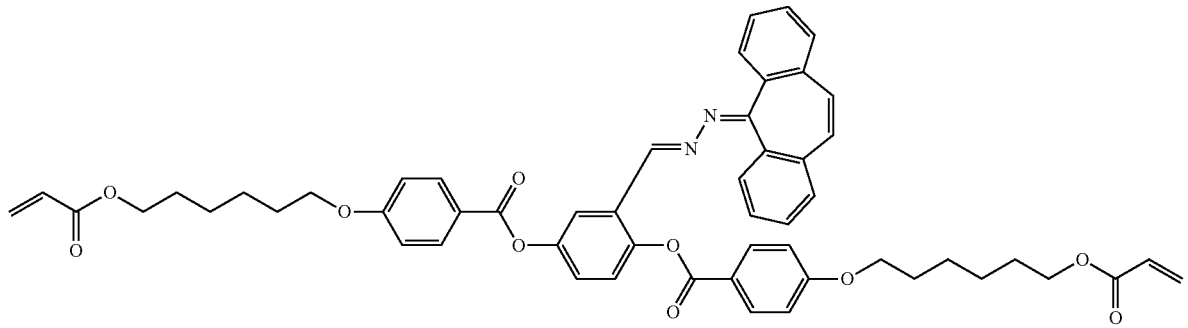

Compound 8

Step 1: Synthesis of Intermediate 1

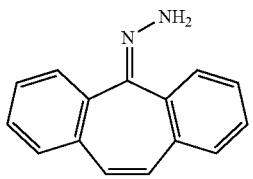 [SMILES: NN=c1c2ccccc2ccc2ccccc12]

Intermediate I

A four-necked reactor equipped with a thermometer was charged with 10 ml (163 mmol) of hydrazine monohydrate and 20 ml of ethylene glycol under a nitrogen stream to effect dissolution. After the addition of 1.5 g (7.3 mmol) of 5H-dibenzo[a,d]cyclohepten-5-one to the solution, 0.1 ml of sulfuric acid was added to the mixture, and the mixture was stirred at 120° C. for 15 hours. The reaction mixture was then cooled to room temperature, added to 100 ml of saturated sodium bicarbonate water, and extracted twice with 100 ml of chloroform. The chloroform layer was washed with 100 ml of a saturated sodium chloride solution, and dried over anhydrous sodium sulfate, and sodium sulfate was filtered off. Chloroform was evaporated from the filtrate under reduced pressure using a rotary evaporator to obtain 1.2 g of an intermediate I as a yellow solid. The solid was then dried, and used directly for the subsequent reaction without purification.

Step 2: Synthesis of Intermediate J

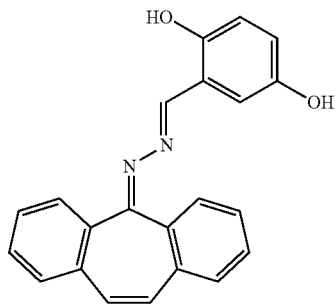 [SMILES: Oc1ccc(O)c(/C=N/N=c2c3ccccc3ccc3ccccc23)c1]

Intermediate J

A four-necked reactor equipped with a thermometer was charged with 1.0 g (4.5 mmol) of the intermediate I synthesized in the step 1, 0.46 g (3.33 mmol) of 2,5-dihydroxybenzaldehyde, and 30 ml of ethanol under a nitrogen stream. After the addition of 0.1 ml of sulfuric acid, the mixture was stirred at 25° C. for 1 hour. After completion of the reaction, the reaction mixture was added to 150 ml of saturated sodium bicarbonate water, and extracted twice with 100 ml of ethyl acetate. The ethyl acetate layer was washed with 150 ml of a saturated sodium chloride solution, and dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=from 85:15 to 80:20 (volume ratio)) to obtain 700 mg of an intermediate J as a yellow solid (yield: 61.8%).

The structure of the target product was identified by $^1$H-NMR.

$^1$H-NMR (400 MHz, CDCl$_3$, TMS, δ ppm): 10.81 (s, 1H), 8.64 (s, 1H), 7.82-7.78 (m, 1H), 7.55-7.40 (m, 7H), 7.30-7.15 (m, 1H), 6.98 (s, 2H), 6.78-6.74 (m, 2H), 6.66-6.64 (m, 1H).

Step 3: Synthesis of Compound 8

A four-necked reactor equipped with a thermometer was charged with 0.7 g (2.06 mmol) of the intermediate J synthesized in the step 1, 1.5 g (5.14 mmol) of 4-(6-acryloyl-hex-1-yloxy)benzoic acid (manufactured by DKSH Japan K.K.), 0.63 g (5.14 mmol) of 4-(dimethylamino)pyridine, and 80 ml of N-methylpyrrolidone under a nitrogen stream. After the addition of 1.18 g (6.17 mmol) of 1-ethyl-3-(3-dimethylaminopropyl)carbodiimide hydrochloride (WSC), the mixture was stirred at 25° C. for 16 hours. After completion of the reaction, the reaction mixture was added to 600 ml of water, and extracted with 250 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=95:5 (volume ratio)) to obtain 1.4 g of a compound 8 as a light yellow solid (yield: 76.4%).

The structure of the target product was identified by $^1$H-NMR.

¹H-NMR (400 MHz, CDCl₃, TMS, δ ppm): 8.64 (s, 1H), 8.13-8.11 (m, 4H), 7.75-7.73 (m, 1H), 7.70 (d, 1H, J=2.8 Hz), 7.46-7.24 (m, 9H), 6.99-6.95 (m, 4H), 6.92 (s, 2H), 6.405 (dd, 1H, J=1.4 Hz, 17.4 Hz), 6.402 (dd, 1H, J=1.4 Hz, 17.4 Hz), 6.13 (dd, 2H, J=10.6 Hz, 17.4 Hz), 5.823 (dd, 1H, J=1.4 Hz, 10.6 Hz), 5.819 (dd, 1H, J=1.4 Hz, 10.6 Hz), 4.18 (t, 4H, J=6.4 Hz), 4.061 (t, 2H, J=6.4 Hz), 4.055 (t, 2H, J=6.4 Hz), 1.88-1.82 (m, 4H), 1.77-1.70 (m, 4H), 1.58-1.44 (m, 8H).

Example 9

Synthesis of Compound 9

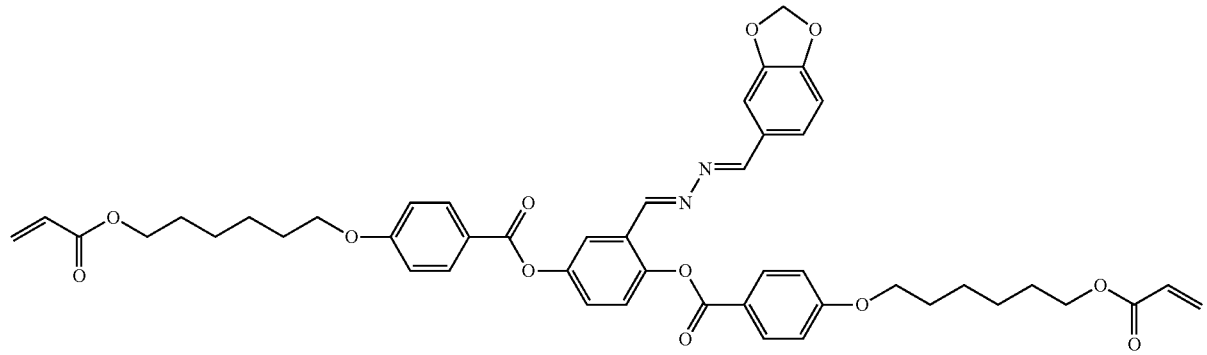

Compound 9

Step 1: Synthesis of Intermediate K

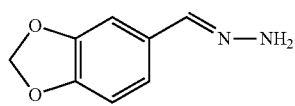 [SMILES: N/N=C/c1ccc2c(c1)OCO2]

Intermediate K

A four-necked reactor equipped with a thermometer was charged with 3.3 g (65.9 mol) of hydrazine monohydrate and 10 ml of ethanol under a nitrogen stream. After the addition of 2.0 g (13.3 mmol) of piperonal (1,3-benzodioxole-5-carbaldehyde) and 10 ml of THF, the mixture was stirred at 25° C. for 1 hour. After completion of the reaction, the reaction mixture was added to 100 ml of saturated sodium bicarbonate water, and extracted twice with 80 ml of chloroform. The chloroform layer was washed with 100 ml of a saturated sodium chloride solution, and dried over anhydrous sodium sulfate, and sodium sulfate was filtered off. Chloroform was evaporated from the filtrate under reduced pressure using a rotary evaporator to obtain 1.3 g of an intermediate K as a light yellow solid. The solid was then dried, and used directly for the subsequent reaction without purification.

Step 2: Synthesis of Compound 9

A four-necked reactor equipped with a thermometer was charged with 1.5 g (2.18 mmol) of the intermediate A synthesized in the step 1 (see Synthesis of compound 1) and 15 ml of THF under a nitrogen stream to effect dissolution. After the addition of a solution prepared by dissolving 448 mg (2.73 mmol) of the intermediate K synthesized in the step 1 in 15 ml of THF, the mixture was stirred at 25° C. for 5 hours. After completion of the reaction, THF was evaporated from the reaction mixture under reduced pressure using a rotary evaporator to obtain a light yellow solid. The light yellow solid was purified by silica gel column chromatography (toluene:ethyl acetate=95:5 (volume ratio)) to obtain 1.2 mg of a compound 9 as a light yellow solid (yield: 66.1%).

The structure of the target product was identified by ¹H-NMR.

¹H-NMR (400 MHz, CDCl³, TMS, δ ppm): 8.74 (s, 1H), 8.44 (s, 1H), 8.19-8.14 (m, 4H), 8.03 (d, 1H, J=2.7 Hz), 7.38-7.29 (m, 3H), 7.14 (dd, 1H, J=1.8 Hz, 8.2 Hz), 7.01-6.96 (m, 4H), 6.82 (d, 1H, J=8.0 Hz), 6.40 (dd, 2H, J=1.4 Hz, 17.4 Hz), 6.12 (dd, 2H, J=10.5 Hz, 17.4 Hz), 6.00 (s, 2H), 5.82 (dd, 2H, J=1.4 Hz, 10.5 Hz), 4.18 (t, 4H, J=6.4 Hz), 4.07 (t, 2H, J=6.4 Hz), 4.05 (t, 2H, J=6.4 Hz), 1.89-1.81 (m, 4H), 1.76-1.70 (m, 4H), 1.56-1.44 (m, 8H).

Example 10

Synthesis of Compound 10

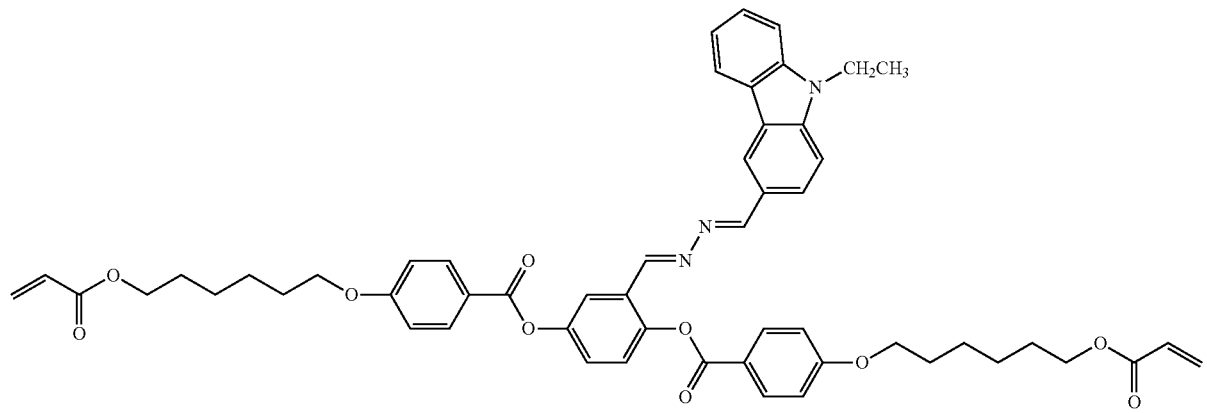

Compound 10

Step 1: Synthesis of Intermediate L

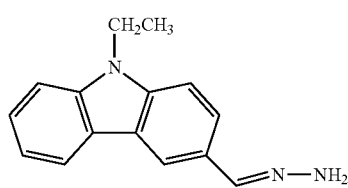 [SMILES: CCn1c2ccccc2c2cc(/C=N/N)ccc21]

Intermediate L

A four-necked reactor equipped with a thermometer was charged with 1.7 g (33.5 mmol) of hydrazine monohydrate and 15 ml of ethanol under a nitrogen stream to effect dissolution. After the addition of a solution prepared by dissolving 1.5 g (6.72 mmol) of N-ethylcarbazole-3-carbaldehyde in 10 ml of THF, the mixture was stirred at 25° C. for 1 hour. After completion of the reaction, the reaction mixture was added to 100 ml of saturated sodium bicarbonate water, and extracted three times with 50 ml of chloroform. The chloroform layer was washed with 100 ml of a saturated sodium chloride solution, and dried over anhydrous sodium sulfate, and sodium sulfate was filtered off. Chloroform was evaporated from the filtrate under reduced pressure using a rotary evaporator to obtain 1.0 g of an intermediate L as a yellow solid. The solid was then dried, and used directly for the subsequent reaction without purification.

Step 2: Synthesis of Compound 10

A four-necked reactor equipped with a thermometer was charged with 2.0 g (2.91 mmol) of the intermediate A synthesized in the step 1 (see Synthesis of compound 1) and 20 ml of THF under a nitrogen stream. After the addition of a solution prepared by dissolving 0.9 g (3.79 mmol) of the intermediate L synthesized in the step 1 in 20 ml of THF, the mixture was stirred at 25° C. for 8 hours. After completion of the reaction, THF was evaporated from the reaction mixture under reduced pressure using a rotary evaporator to obtain a yellow solid. The yellow solid was purified by silica gel column chromatography (toluene:ethyl acetate=90:10 (volume ratio)) to obtain 1.7 g of a compound 10 as a yellow solid (yield: 64.5%).

The structure of the target product was identified by $^1$H-NMR.

$^1$H-NMR (400 MHz, CDCl$_3$, TMS, δ ppm): 8.85 (s, 1H), 8.76 (s, 1H), 8.50 (d, 1H, J=1.4 Hz), 8.22-8.16 (m, 4H), 8.12 (d, 1H, J=7.8 Hz), 8.09 (d, 1H, J=2.8 Hz), 7.91 (dd, 1H, J=1.4 Hz, 8.3 Hz), 7.49 (m, 1H), 7.43-7.24 (m, 5H), 7.03-6.97 (m, 4H), 6.410 (dd, 1H, J=1.4 Hz, 17.4 Hz), 6.407 (dd, 1H, J=1.4 Hz, 17.4 Hz), 6.129 (dd, 1H, J=10.5 Hz, 17.4 Hz), 6.126 (dd, 1H, J=10.5 Hz, 17.4 Hz), 5.827 (dd, 1H, J=1.4 Hz, 10.5 Hz), 5.817 (dd, 1H, J=1.4 Hz, 10.5 Hz), 4.37 (q, 2H, J=7.4 Hz), 4.19 (t, 4H, J=6.4 Hz), 4.08 (t, 2H, J=6.4 Hz), 4.06 (t, 2H, J=6.4 Hz), 1.90-1.82 (m, 4H), 1.77-1.70 (m, 4H), 1.59-1.42 (m, 8H), 1.44 (t, 3H, J=7.4 Hz).

Example 11

Synthesis of Compound 11

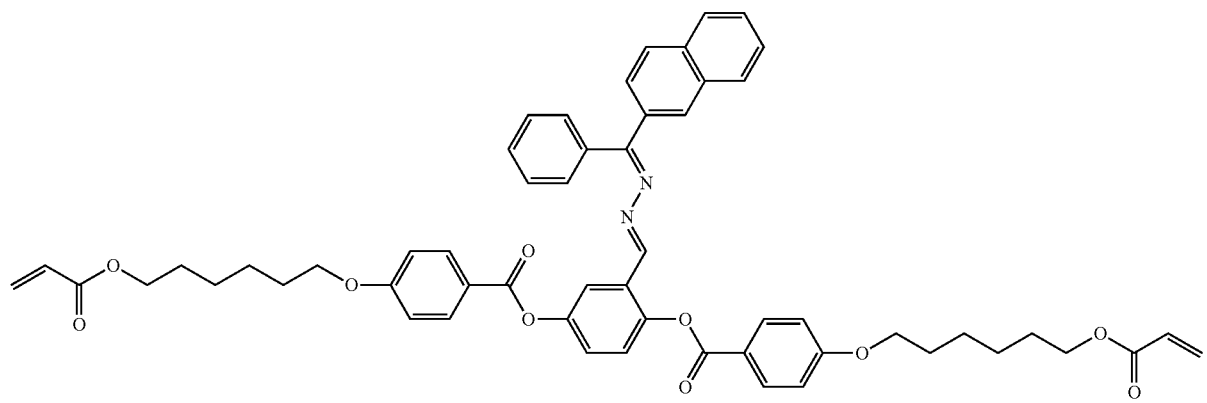

Compound 11

Step 1: Synthesis of Intermediate M

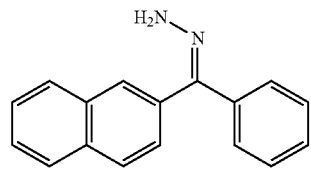 [SMILES: N/N=C(/c1ccccc1)c1ccc2ccccc2c1]

Intermediate M

A four-necked reactor equipped with a thermometer was charged with 1.6 ml (32.3 mmol) of hydrazine monohydrate and 15 ml of ethanol under a nitrogen stream. After the addition of 1.50 g (6.46 mmol) of 2-naphthyl phenyl ketone, the mixture was refluxed for 6 hours with heating. After completion of the reaction, the reaction mixture was added to 50 ml of saturated sodium bicarbonate water, and extracted twice with 50 ml of chloroform. The chloroform layer was washed with 50 ml of a saturated sodium chloride solution, and dried over anhydrous sodium sulfate, and sodium sulfate was filtered off. Chloroform was evaporated from the filtrate under reduced pressure using a rotary evaporator to obtain 1.55 g of an intermediate M as a yellow solid. The solid was then dried, and used directly for the subsequent reaction without purification.

Step 2: Synthesis of Compound 11

A four-necked reactor equipped with a thermometer was charged with 4.44 g (6.46 mmol) of the intermediate A synthesized in the step 1 (see Synthesis of compound 1), 1.55 g (6.46 mmol) of the intermediate M synthesized in the step 1, and 15 ml of propanol under a nitrogen stream, and the mixture was refluxed for 8 hours with heating. After completion of the reaction, the reaction mixture was added to 100 ml of saturated sodium bicarbonate water, and extracted twice with 100 ml of chloroform. The chloroform layer was washed with 100 ml of a saturated sodium chloride solution, and dried over anhydrous sodium sulfate, and sodium sulfate was filtered off. Chloroform was evaporated from the filtrate under reduced pressure using a rotary evaporator to obtain a yellow solid. The yellow solid was purified by silica gel column chromatography (toluene:ethyl acetate=95:5 (volume ratio)) to obtain 3.19 g of a compound 11 as a yellow solid (yield: 54.0%).

The structure of the target product was identified by $^1$H-NMR (underlined parts: stereoisomer).

$^1$H-NMR (500 MHz, CDCl$_3$, TMS, δ ppm): 8.75 (s, 1H), 8.71 (s, 1H), 8.16 (d, 2H, J=9.0 Hz), 8.12 (d, 2H+2H, J=9.0 Hz), 8.05 (d, 2H, J=9.0 Hz), 7.98 (dd, 1H, J=2.0 Hz, 8.5 Hz), 7.91 (s, 1H), 7.76-7.85 (m, 3H+4H), 7.66-7.72 (m, 3H+1H), 7.41-7.51 (m, 2H+7H), 7.25-7.39 (m, 5H+3H), 6.98 (d, 2H, J=9.0 Hz), 6.97 (d, 2H, J=9.0 Hz), 6.94 (d, 2H, J=9.0 Hz), 6.93 (d, 2H, J=9.0 Hz), 6.38-6.43 (m, 2H+2H), 6.09-6.16 (m, 2H+2H), 5.80-5.84 (m, 2H+2H), 4.17-4.20 (m, 4H+4H), 4.02-4.07 (m, 4H+4H), 1.82-1.88 (m, 4H+4H), 1.70-1.76 (m, 4H+4H), 1.42-1.57 (m, 8H+8H).

Example 12

Synthesis of Compound 12

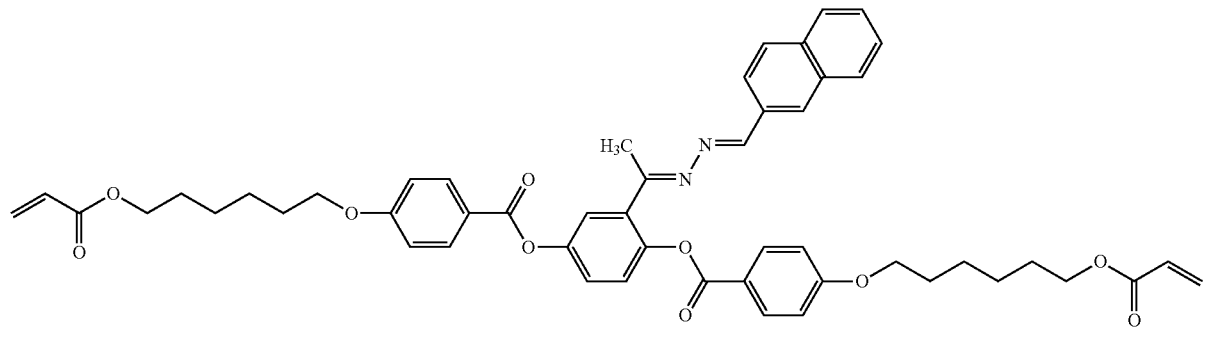

Compound 12

Step 1: Synthesis of Intermediate N

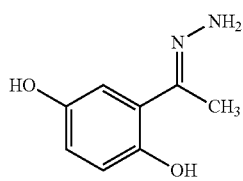

Intermediate N

A four-necked reactor equipped with a thermometer was charged with 9.6 ml (197 mmol) of hydrazine monohydrate and 20 ml of propanol under a nitrogen stream. After the addition of 3.00 g (19.7 mmol) of 2',5'-dihydroxyacetophenone, the mixture was stirred at 25° C. for 2 hours. After completion of the reaction, the reaction mixture was added to 50 ml of saturated sodium bicarbonate water, and extracted twice with 50 ml of chloroform. The chloroform layer was washed with 50 ml of a saturated sodium chloride solution, and dried over anhydrous sodium sulfate, and sodium sulfate was filtered off. Chloroform was evaporated from the filtrate under reduced pressure using a rotary evaporator to obtain 2.86 g of an intermediate N as a light yellow solid. The solid was then dried, and used directly for the subsequent reaction without purification.

Step 2: Synthesis of Intermediate O

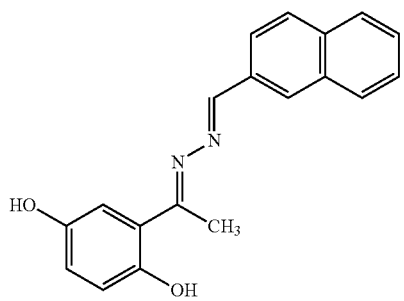 [SMILES: C/C(=N\N=C\c1ccc2ccccc2c1)c1cc(O)ccc1O]

Intermediate O

A four-necked reactor equipped with a thermometer was charged with a solution prepared by dissolving 1.00 g (6.02 mmol) of the intermediate N synthesized in the step 1 and 940 mg (6.02 mmol) of 2-naphthaldehyde in 15 ml of propanol under a nitrogen stream, and the mixture was stirred at 25° C. for 5 hours. After completion of the reaction, the reaction mixture was added dropwise to 200 ml of water to precipitate a solid. The solid was filtered off by suction filtration. The solid was then washed with water, and air-dried to obtain 1.80 of an intermediate O as a yellow solid. The intermediate O was used directly for the subsequent reaction without purification.

Step 3: Synthesis of Compound 12

A four-necked reactor equipped with a thermometer was charged with 1.00 g (3.29 mmol) of the intermediate 0 synthesized in the step 2, 2.40 g (8.21 mmol) of 4-(6-acryloyl-hex-1-yloxy)benzoic acid (manufactured by DKSH Japan K.K.), 120 m (987 μmol) of 4-(dimethylamino)pyridine, and 30 ml of N-methylpyrrolidone under a nitrogen stream. After the addition of 1.57 g (8.21 mmol) of 1-ethyl-3-(3-dimethylaminopropyl)carbodiimide hydrochloride (WSC), the mixture was stirred at 25° C. for 18 hours. After completion of the reaction, the reaction mixture was added to 300 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=75:25 (volume ratio)) to obtain 1.14 g of a compound 12 as a light yellow solid (yield: 40.6%).

The structure of the target product was identified by $^1$H-NMR.

$^1$H-NMR (400 MHz, CDCl$_3$, TMS, δ ppm): 8.25 (s, 1H), 8.15 (d, 4H, J=9.2 Hz), 8.01 (d, 1H, J=8.2 Hz), 7.92 (s, 1H), 7.82-7.86 (m, 3H), 7.48-7.58 (m, 3H), 7.29-7.35 (m, 2H), 6.96 (d, 4H, J=9.2 Hz), 6.40 (d, 1H, J=17.5 Hz), 6.39 (d, 1H, J=17.4 Hz), 6.12 (dd, 1H, J=10.5 Hz, 17.5 Hz), 6.10 (dd, 1H, J=10.5 Hz, 17.4 Hz), 5.82 (d, 1H, J=10.5 Hz), 5.80 (d, 1H, J=10.5 Hz), 4.18 (t, 2H, J=6.9 Hz), 4.15 (t, 2H, J=6.4 Hz), 4.05 (t, 2H, J=6.4 Hz), 4.01 (t, 2H, J=6.4 Hz), 2.48 (s, 3H), 1.76-1.88 (m, 4H), 1.66-1.74 (m, 4H), 1.41-1.57 (m, 8H).

Example 13

Synthesis of Compound 13

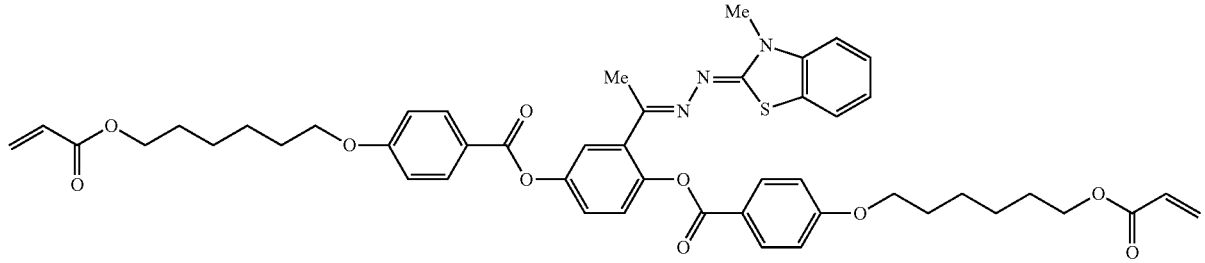

Compound 13

Step 1: Synthesis of Intermediate P

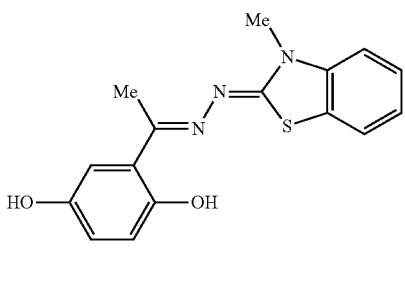 [SMILES: C/C(=N\N=c1/sc2ccccc2n1C)c1cc(O)ccc1O]

Intermediate P

A four-necked reactor equipped with a thermometer was charged with 2 g (13.14 mmol) of 2,5-dihydroxyacetophenone, 3.4 g (15.77 mmol) of 3-methyl-2-benzothiazolinone-hydrazone hydrochloride hydrate, and 70 ml of 1-propanol under a nitrogen stream, and the mixture was refluxed for 2 hours with heating. After completion of the reaction, the reaction mixture was returned to 25° C. to precipitate a solid. The solid was filtered off, and washed with 1-propanol to obtain 2.8 g of an intermediate P as an orange solid (yield: 68.0%).

The structure of the target product was identified by $^1$H-NMR.

$^1$H-NMR (500 MHz, DMSO-d$_6$, TMS, δ ppm): 12.2-11.9 (br, 2H), 7.71 (dd, 1H, J=1.0 Hz, 7.5 Hz), 7.40-7.34 (m, 2H), 7.15-7.12 (m, 1H), 7.00-6.99 (m, 1H), 6.75-6.74 (m, 2H), 3.63 (s, 3H), 2.53 (s, 3H).

Step 2: Synthesis of Intermediate Q

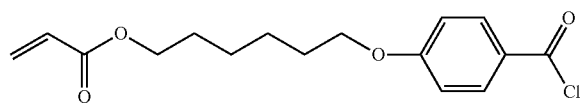 [SMILES: C=CC(=O)OCCCCCCOc1ccc(C(=O)Cl)cc1]

Intermediate Q

A four-necked reactor equipped with a thermometer was charged with 5 g (17.10 mmol) of 4-(6-acryloyl-hex-1-yloxy) benzoic acid (manufactured by DKSH Japan K.K.) and 200 ml of THF under a nitrogen stream to prepare a homogeneous solution. 21.7 g (0.17 mol) of oxalyl chloride was slowly added dropwise to the solution while adjusting the temperature of the reaction mixture at 20° C. or less, and the mixture was stirred at 23° C. for 18 hours. After completion of the reaction, THF and the residual oxalyl chloride were evaporated from the reaction mixture under reduced pressure using a rotary evaporator to obtain a light yellow solid. The solid was used directly for the subsequent reaction without purification.

Step 3: Synthesis of Compound 13

A four-necked reactor equipped with a thermometer was charged with 2.0 g (6.38 mmol) of the intermediate P synthesized in the step 1, 2.5 g (19.14 mmol) of diisopropylethylamine, 234 mg (1.91 mmol) of 4-(dimethylamino)pyridine, and 80 ml of THF under a nitrogen stream to prepare a homogeneous solution. A solution prepared by dissolving 5.9 g (19.14 mmol) of the intermediate Q synthesized in the step 2 in 100 ml of THF was slowly added dropwise to the solution in an ice bath. After the dropwise addition, the mixture was stirred for 30 minutes in an ice bath, and stirred at 23° C. for 4 hours. After completion of the reaction, the reaction mixture was added to 500 ml of dilute hydrochloric acid, and extracted twice with 200 ml of ethyl acetate. The ethyl acetate layer was washed with a saturated sodium chloride solution, and dried over anhydrous sodium sulfate, and sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=9:1 (volume ratio)) to obtain 1.1 g of a compound 13 as a light yellow solid (yield: 20.0%).

The structure of the target product was identified by $^1$H-NMR.

$^1$H-NMR (500 MHz, CDCl$_3$, TMS, δ ppm): 8.18-8.14 (m, 4H), 7.56 (dd, 1H, J=1.0 Hz, 2.0 Hz), 7.34 (dd, 1H, J=1.0 Hz, 7.5 Hz), 7.28-7.21 (m, 2H), 7.03-6.92 (m, 7H), 4.609 (dd, 1H, J=1.5 Hz, 17.5 Hz), 6.404 (dd, 1H, J=1.5 Hz, 17.5 Hz), 6.130 (dd, 1H, J=10.5 Hz, 17.5 Hz), 6.125 (dd, 1H, J=10.5 Hz, 17.5 Hz), 5.827 (dd, 1H, J=1.5 Hz, 10.5 Hz), 5.823 (dd, 1H, J=1.5 Hz, 10.5 Hz), 4.19 (t, 2H, J=6.5 Hz), 4.18 (t, 2H, J=6.5 Hz), 4.06 (t, 2H, J=6.5 Hz), 4.02 (t, 2H, J=6.5 Hz), 3.55 (s, 3H), 2.41 (s, 3H), 1.88-1.79 (m, 4H), 1.76-1.68 (m, 4H), 1.58-1.45 (m, 8H).

Synthesis Example 1

Synthesis of Compound A

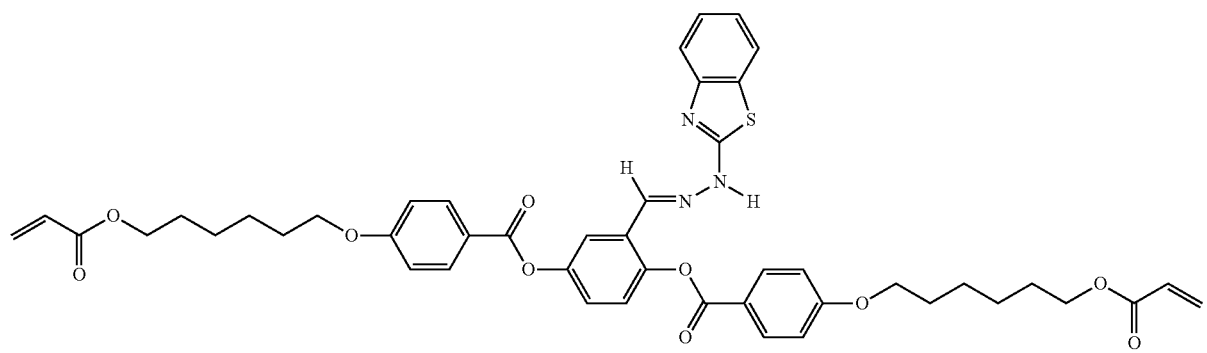

Compound A

A four-necked reactor equipped with a thermometer was charged with 10.5 g (15.3 mmol) of the intermediate A synthesized in the step 1 (see Example 1), 3.0 g (18.3 mmol) of 2-hydrazinobenzothiazole, and 80 ml of THF under a nitrogen stream to prepare a homogeneous solution. After the addition of 18 mg (0.08 mmol) of (±)-10-camphorsulfonic acid, the mixture was stirred at 25° C. for 3 hours. After completion of the reaction, the reaction mixture was added to 800 ml of 10% sodium bicarbonate water, and extracted twice with 100 ml of ethyl acetate. The ethyl acetate layer was collected, and dried over anhydrous sodium sulfate, and sodium sulfate was filtered off. Ethyl acetate was evaporated from the filtrate under reduced pressure using a rotary evaporator to obtain a light yellow solid. The light yellow solid was purified by silica gel column chromatography (toluene:ethyl acetate=8:2 (volume ratio)) to obtain 8.0 g of a compound A as a light yellow solid (yield: 62.7%).

The structure of the target product was identified by $^1$H-NMR and mass spectroscopy.

$^1$H-NMR (500 MHz, DMSO-$d_6$, TMS, δ ppm): 12.30 (br, 1H), 8.19 (s, 1H), 8.17-8A2 (m, 4H), 7.76 (d, 1H, J=3.0 Hz), 7.68 (d, 1H, J=7.5 Hz), 7.45-7.39 (m, 3H), 7.28 (t, 1H, J=8.0 Hz), 7.18-7.14 (m, 4H), 7.09 (t, 1H, J=8.0 Hz), 6.33 (dd, 2H, J=1.5 Hz, 17.5 Hz), 6.18 (dd, 2H, J=10.5 Hz, 17.5 Hz), 5.944 (dd, 1H, J=1.5 Hz, 10.5 Hz), 5.941 (dd, 1H, J=1.5 Hz, 10.5 Hz), 4.14-4.10 (m, 8H), 1.80-1.75 (m, 4H), 1.69-1.63 (m, 4H), 1.53-1.38 (m, 8H).

LCMS (APCI): calcd for $C_{46}H_{47}N_3O_{10}S$: 833 [M$^+$]. Found: 833.

The phase transition temperature was measured by the following method using the compounds 1 to 13 obtained in Examples 1 to 13, the compound A obtained in Synthesis Example 1, the compound 1r obtained in Reference Example 1 that was used in Comparative Example 1 ("K35" manufactured by Zeon Corporation), and the compound 2r obtained in Reference Example 2 that was used in Comparative Example 2 ("LC242" manufactured by BASF).

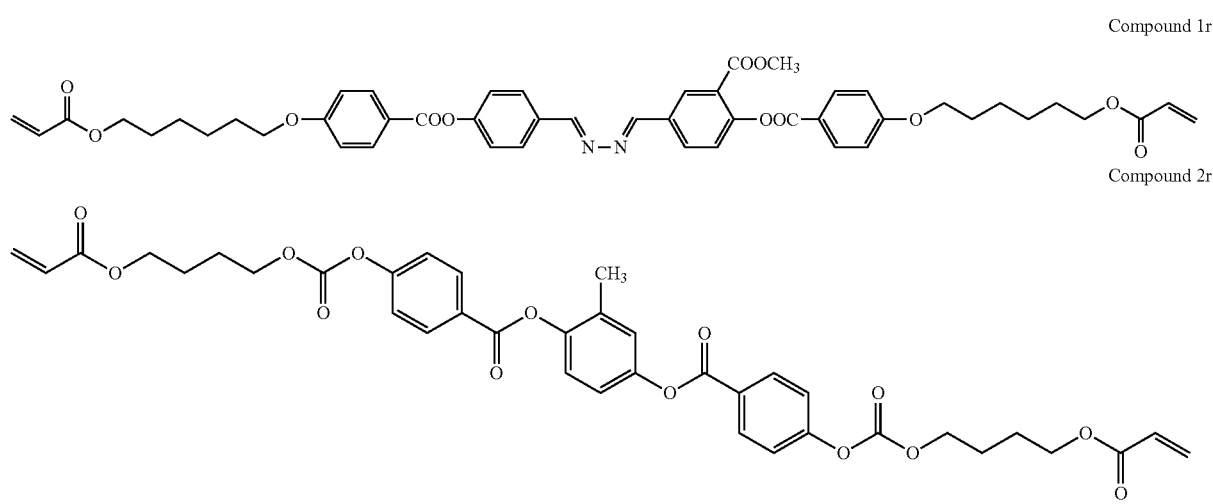

Compound 1r

Compound 2r

Measurement of Phase Transition Temperature 10 mg of each compound (compounds 1 to 13, compound A obtained in Synthesis Example 1, compound 1r obtained in Reference Example 1, and compound 2r obtained in Reference Example 2) was weighed, and placed in a solid state between two glass substrates provided with a polyimide alignment film subjected to a rubbing treatment. The substrates were heated from 50° C. to 200° C. on a hot plate, and then cooled to 50° C. A change in structure during a change in temperature was observed using a polarizing optical microscope ("ECLIPSE LV100POL" manufactured by Nikon Corporation).

The phase transition temperature measurement results are shown in Table 1.

In Table 1, "C" indicates "crystal", "N" indicates "nematic", and "I" indicates "isotropic". The term "crystal" means that the test compound was in a solid phase, the term "nematic" means that the test compound was in a nematic liquid crystal phase, and the term "isotropic" means that the test compound was in an isotropic liquid phase.

TABLE 1

| | Polymerizable compound | Phase transition temperature |
|---|---|---|
| Example 1 | Compound 1 | C ⇌ N ⇌ I; 50° C. or less, 109° C., 129° C. |
| Example 2 | Compound 2 | C ⇌ N ⇌ I; 50° C. or less, 84° C., 138° C. |
| Example 3 | Compound 3 | C ⇌ N ⇌ I; 50° C. or less, 51° C., 115° C. |
| Example 4 | Compound 4 | C ⇌ N ⇌ I; 50° C. or less, 80° C., 110° C. |
| Example 5 | Compound 5 | C ⇌ N ⇌ I; 50° C. or less, 71° C., 121° C. |
| Example 6 | Compound 6 | C ⇌ N ⇌ I; 50° C. or less, 55° C., 143° C. |
| Example 7 | Compound 7 | C ⇌ N ⇌ I; 50° C. or less, 76° C., 128° C. |
| Example 8 | Compound 8 | C ⇌ N ⇌ I; 30° C. or less, 90° C., 123° C. |
| Example 9 | Compound 9 | C ⇌ N ⇌ I; 50° C. or less, 67° C., 97° C. |
| Example 10 | Compound 10 | C ⇌ N ⇌ I; 50° C. or less, 50° C., 119° C. |
| Example 11 | Compound 11 | C ⇌ N ⇌ I; 50° C. or less, 65° C., 73° C., 78° C. |

TABLE 1-continued

| | Polymerizable compound | Phase transition temperature |
|---|---|---|
| Example 12 | Compound 12 | C ⇌ N ⇌ I; 50° C. or less, 50° C. or less, 82° C. |
| Example 13 | Compound 13 | C ⇌ I; 50° C. or less, 122° C. |
| Synthesis Example 1 | Compound A | C ⇌ N ⇌ I; 50° C. or less, 102° C., 140° C., 165° C. |
| Reference Example 1 | Compound 1r | C ⇌ N → I; 50° C. or less, 80° C., 200° C. or more |
| Reference Example 2 | Compound 2r | C ⇌ N ⇌ I; 50° C. or less, 60° C., 122° C., 123° C. |

Examples 14 to 25 and Comparative Examples 1 and 2

1 g of each compound (compounds 1 to 12 obtained in Examples 1 to 12, compound 1r, and compound 2r), 30 mg of Irgacure 907 (manufactured by BASF) (photoinitiator), and 100 mg of a 1% cyclopentanone solution of KH-40 (manufactured by AGC Seimi Chemical Co., Ltd.) (surfactant) were dissolved in cyclopentanone (see Table 2). The solution was filtered through a disposable filter having a pore size of 0.45 µm to obtain a polymerizable compositions (polymerizable compositions 1 to 12, 1r, and 2r).

Example 26

130.5 g of the compound obtained in Example 13, 0.5 g of the compound A obtained in Synthesis Example 1, 30 mg of Irgacure 907 (manufactured by BASF) (photoinitiator), and 100 mg of a 1% cyclopentanone solution of KH-40 (manufactured by AGC Seimi Chemical Co., Ltd.) (surfactant) were dissolved in 2.33 g of cyclopentanone. The solution was filtered through a disposable filter having a pore size of 0.45 µm to obtain a polymerizable composition 13.

The polymerizable compositions 1 to 13, 1r, and 2r were polymerized to obtain polymers. The retardation was measured, and the wavelength dispersion was evaluated using the resulting polymers.

Measurement of Retardation and Evaluation of Wavelength Dispersion (i) Preparation of Transparent Resin Substrate Provided with Alignment Film Each side of an alicyclic olefin polymer film ("Zeonor Film ZF16-100" manufactured by Zeon Corporation) (thickness: 100 µm) was subjected to a corona discharge treatment. A 5% polyvinyl alcohol aqueous solution was applied to one side of the film using a #2 wire bar, and the film was dried to form an alignment film having a thickness of 0.1 µm. The alignment film was subjected to a rubbing treatment to prepare a transparent resin substrate on which the alignment film was formed.

(ii) Formation of Liquid Crystal Layer Using Polymerizable Composition

Each polymerizable composition (polymerizable compositions 1 to 13, 1r, and 2r) was applied to the surface of the transparent resin substrate on which the alignment film was formed, using a #4 wire bar. The film was dried for 30 seconds at the temperature shown in Table 2, and subjected to an alignment treatment for 3 minutes at the temperature shown in Table 2 to form a liquid crystal layer having a thickness of about 1 µm. UV rays were applied to the liquid crystal layer at a dose of 2000 mJ/cm² to effect polymerization to prepare a wavelength dispersion measurement sample.

(iii) Measurement of Retardation

The retardation between 400 nm and 800 nm was measured using the sample utilizing an ellipsometer ("XLS-100" manufactured by J. A. Woollam).

(iv) Evaluation of Wavelength Dispersion

The wavelength dispersion was evaluated based on the values α and β calculated by the following expressions using the measured retardation.

α=(retardation at 449.9 nm)/(retardation at 548.5 nm) [Expression 1]

β=(retardation at 650.2 nm)/(retardation at 548.5 nm) [Expression 2]

The wavelength dispersion evaluation results are shown in Table 2.

The value α is smaller than 1, and the value β is larger than 1 when ideal wideband wavelength dispersion (reverse wavelength dispersion) is achieved. The values α and β are almost identical when flat wavelength dispersion is achieved. The value α is larger than 1, and the value β is smaller than 1 when normal dispersion is achieved.

Specifically, flat wavelength dispersion that ensures that the values α and β are almost identical is preferable, and reverse wavelength dispersion that ensures that the value α is smaller than 1, and the value β is larger than 1 is particularly preferable.

TABLE 2

|  | Polymerizable compound | Cyclopentanone (g) | Drying temperature (° C.) | Alignment temperature (° C.) | α | β |
| --- | --- | --- | --- | --- | --- | --- |
| Example 14 | Compound 1 | 4.00 | 135 | 80 | 0.814 | 1.046 |
| Example 15 | Compound 2 | 4.00 | 145 | 65 | 0.883 | 0.857 |
| Example 16 | Compound 3 | 2.33 | 125 | 40 | 1.018 | 0.987 |
| Example 17 | Compound 4 | 2.33 | 120 | 65 | 0.882 | 0.974 |
| Example 18 | Compound 5 | 2.33 | 130 | 65 | 1.038 | 0.986 |
| Example 19 | Compound 6 | 3.17 | 150 | 45 | 1.034 | 1.000 |
| Example 20 | Compound 7 | 3.00 | 135 | 65 | 1.018 | 0.997 |
| Example 21 | Compound 8 | 2.33 | 135 | 65 | 1.013 | 0.984 |
| Example 22 | Compound 9 | 2.33 | 110 | 50 | 1.000 | 0.991 |
| Example 23 | Compound 10 | 2.33 | 125 | 40 | 1.009 | 0.991 |
| Example 24 | Compound 11 | 2.33 | 70 | 45 | 1.011 | 0.999 |
| Example 25 | Compound 12 | 2.33 | 90 | 23 | 1.007 | 0.984 |
| Example 26 | Compound 13 + Compound A | 2.33 | 100 | 23 | 1.011 | 0.997 |
| Comparative Example 1 | Compound 1r | 2.33 | 90 | 23 | 1.193 | 0.918 |
| Comparative Example 2 | Compound 2r | 2.33 | 80 | 23 | 1.086 | 0.970 |

As is clear from the results shown in Table 2, it was confirmed that optically anisotropic articles (polymers) were obtained in Examples 14 to 26. The values α and β were almost identical when using the optically anisotropic articles obtained in Examples 14 to 26. In Example 14, the value α was smaller than 1, and the value β was larger than 1 (i.e., particularly preferable results were obtained).

In Comparative Examples 1 and 2, the value α was significantly larger than 1, and the value β was smaller than 1.

The invention claimed is:

1. A polymerizable compound represented by a formula (I),

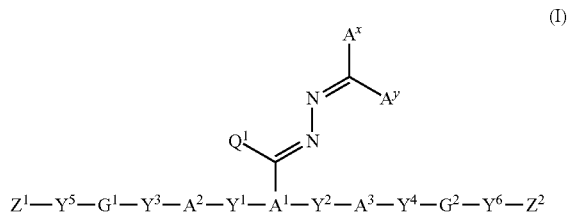

$Z^1$—$Y^5$—$G^1$—$Y^3$—$A^2$—$Y^1$—$A^1$—$Y^2$—$A^3$—$Y^4$—$G^2$—$Y^6$—$Z^2$ wherein $Y^1$ to $Y^6$ are independently a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ is a hydrogen atom or an alkyl group having 1 to 6 carbon atoms, $G^1$ and $G^2$ are independently a substituted or unsubstituted divalent aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the aliphatic group includes two or more adjacent —O— or —S— is excluded, $R^2$ is a hydrogen atom or an alkyl group having 1 to 6 carbon atoms, $Z^1$ and $Z^2$ are independently an alkenyl group having 2 to 10 carbon atoms that is substituted with a halogen atom, or unsubstituted, $A^x$ is an organic group having 2 to 30 carbon atoms that includes at least one aromatic ring selected from a group consisting of an aromatic hydrocarbon ring and an aromatic hetero ring, $A^y$ is a hydrogen atom, a substituted or unsubstituted alkyl group having 1 to 6 carbon atoms, or an organic group having 2 to 30 carbon atoms that includes at least one aromatic ring selected from a group consisting of an aromatic hydrocarbon ring and an aromatic hetero ring, provided that the aromatic ring included in $A^x$ and $A^y$ is substituted or unsubstituted, and $A^x$ and $A^y$ optionally bond to each other to form a ring, $A^1$ is a substituted or unsubstituted trivalent aromatic group, $A^2$ and $A^3$ are independently a substituted or unsubstituted divalent aromatic group having 6 to 30 carbon atoms, and $Q^1$ is a hydrogen atom, or a substituted or unsubstituted alkyl group having 1 to 6 carbon atoms.

2. The polymerizable compound according to claim 1, wherein a total number of π electrons included in $A^x$ and $A^y$ is 4 to 24.

3. The polymerizable compound according to claim 1, wherein $A^1$ is a substituted or unsubstituted trivalent benzene ring, or a substituted or unsubstituted trivalent naphthalene ring, and $A^2$ and $A^3$ are independently a substituted or unsubstituted phenylene group, or a substituted or unsubstituted naphthylene group.

4. The polymerizable compound according to claim 1, wherein $Y^1$ to $Y^6$ are independently a chemical single bond, —O—, —O—C(=O)—, —C(=O)—O—, or —O—C(=O)—O—.

5. The polymerizable compound according to claim 1, wherein $Z^1$ and $Z^2$ are independently $CH_2$=CH—, $CH_2$=C($CH_3$)—, or $CH_2$=C(Cl)—.

6. The polymerizable compound according to claim 1, wherein $G^1$ and $G^2$ are independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more adjacent —O— is excluded.

7. The polymerizable compound according to claim 1, wherein $G^1$ and $G^2$ are independently a divalent alkylene group having 1 to 12 carbon atoms.

8. A polymerizable composition comprising the polymerizable compound according to claim 1, and an initiator.

9. A polymer obtained by polymerizing the polymerizable compound according to claim 1.

10. An optically anisotropic article comprising the polymer according to claim 9.

11. The polymerizable compound according to claim 2, wherein $A^1$ is a substituted or unsubstituted trivalent benzene ring, or a substituted or unsubstituted trivalent naphthalene ring, and $A^2$ and $A^3$ are independently a substituted or unsubstituted phenylene group, or a substituted or unsubstituted naphthylene group.

12. The polymerizable compound according to claim 2, wherein $Y^1$ to $Y^6$ are independently a chemical single bond, —O—, —O—C(=O)—, —C(=O)—O—, or —O—C(=O)—O—.

13. The polymerizable compound according to claim 3, wherein $Y^1$ to $Y^6$ are independently a chemical single bond, —O—, —O—C(=O)—, —C(=O)—O—, or —O—C(=O)—O—.

14. The polymerizable compound according to claim 2, wherein $Z^1$ and $Z^2$ are independently $CH_2$=CH—, $CH_2$=C($CH_3$)—, or $CH_2$=C(Cl)—.

15. The polymerizable compound according to claim 3, wherein $Z^1$ and $Z^2$ are independently $CH_2$=CH—, $CH_2$=C($CH_3$)—, or $CH_2$=C(Cl)—.

16. The polymerizable compound according to claim 4, wherein $Z^1$ and $Z^2$ are independently $CH_2$=CH—, $CH_2$=C($CH_3$)—, or $CH_2$=C(Cl)—.

17. The polymerizable compound according to claim 2, wherein $G^1$ and $G^2$ are independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more adjacent —O— is excluded.

18. The polymerizable compound according to claim 3, wherein $G^1$ and $G^2$ are independently a substituted or unsubstituted divalent aliphatic group having 1 to 12 carbon atoms that optionally includes —O—, —O—C(=O)—, —C(=O)—O—, or —C(=O)—, provided that a case where the aliphatic group includes two or more adjacent —O— is excluded.

19. A polymer obtained by polymerizing the polymerizable composition according to claim 8.

20. An optically anisotropic article comprising the polymer according to claim 19.

* * * * *